US009957317B2

(12) United States Patent
West et al.

(10) Patent No.: US 9,957,317 B2
(45) Date of Patent: May 1, 2018

(54) HUMANIZED ANTI-TAU ANTIBODIES

(71) Applicant: C2N Diagnostics, LLC, Saint Louis, MO (US)

(72) Inventors: Tim West, Saint Louis, MO (US); Diljeet S. Athwal, Slough (GB); Timothy D. Jones, Cambridgeshire (GB); Francis J. Carr, Aberdeen (GB); Robert George Edward Holgate, Royston (GB)

(73) Assignee: C2N Diagnostics, LLC, Saint Louis, MO (US)

( * ) Notice: Subject to any disclaimer, the term of this patent is extended or adjusted under 35 U.S.C. 154(b) by 16 days.

(21) Appl. No.: 15/257,086

(22) Filed: Sep. 6, 2016

(65) Prior Publication Data

US 2017/0058024 A1    Mar. 2, 2017

Related U.S. Application Data

(63) Continuation of application No. PCT/US2015/038002, filed on Jun. 26, 2015.

(60) Provisional application No. 62/170,036, filed on Jun. 2, 2015, provisional application No. 62/080,903, filed on Nov. 17, 2014, provisional application No. 62/018,436, filed on Jun. 27, 2014.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,492,812 A | 2/1996 | Vooheis |
| 5,601,985 A | 2/1997 | Trojanowski et al. |
| 6,121,003 A | 9/2000 | Vanmechelen et al. |
| 6,589,746 B1 | 7/2003 | Zemlan |
| 6,797,478 B1 | 9/2004 | Zemlan et al. |
| 6,900,293 B2 | 5/2005 | Mercken et al. |
| 7,238,788 B2 | 7/2007 | Lee |
| 7,348,157 B2 | 3/2008 | Eriksson et al. |
| 7,442,516 B2 | 10/2008 | Ohno et al. |
| 7,446,180 B2 | 11/2008 | Novak |
| 7,728,109 B2 | 6/2010 | Kikly |
| 8,012,936 B2 | 9/2011 | Sigurdsson et al. |
| 8,084,584 B2 | 12/2011 | Sugo et al. |
| 8,318,917 B2 | 11/2012 | Taylor et al. |
| 8,673,949 B2 | 3/2014 | Albright et al. |
| 8,697,076 B2 | 4/2014 | Binder et al. |
| 8,703,137 B2 | 4/2014 | Chain |
| 8,748,386 B2 | 6/2014 | Sigurdsson |
| 8,778,343 B2 | 7/2014 | Kayed |
| 8,895,714 B2 | 11/2014 | Tickle et al. |
| 8,926,974 B2 | 1/2015 | Griswold-Prenner et al. |
| 8,980,270 B2 | 3/2015 | Griswold-Prenner et al. |
| 8,980,271 B2 | 3/2015 | Griswold-Prenner et al. |
| 9,051,367 B2 | 6/2015 | Griswold-Prenner et al. |
| 9,161,520 B2 | 10/2015 | Kontsekova et al. |
| 9,351,986 B2 | 5/2016 | Kunz et al. |
| 2002/0086009 A1 | 7/2002 | Koichi et al. |
| 2002/0018266 A1 | 12/2002 | Fong |
| 2002/0018810 A1 | 12/2002 | Mandelkow et al. |
| 2002/0188106 A1 | 12/2002 | Mandelkow et al. |
| 2006/0167227 A1 | 7/2006 | Kontsekova et al. |
| 2006/0251645 A1* | 11/2006 | Co ........................ A61K 39/395 424/141.1 |
| 2007/0134724 A1 | 6/2007 | Davis et al. |
| 2008/0220449 A1 | 9/2008 | Vasan et al. |
| 2010/0009388 A1 | 1/2010 | An et al. |
| 2010/0047257 A1* | 2/2010 | Blanc ................. C07K 16/2866 424/174.1 |
| 2010/0284909 A1 | 11/2010 | Wisniewski et al. |
| 2010/0316564 A1 | 12/2010 | Sigurdsson |

(Continued)

FOREIGN PATENT DOCUMENTS

AU    2013205313 A1    5/2013
CN    101307108 L    11/2008

(Continued)

OTHER PUBLICATIONS

Office Action for Chinese Application No. 201380045706.3, dated Dec. 21, 2016.
Frost et al., "Prion-like Mechanisms in Neurodegenerative Diseases", Nat Rev Neurosci., 2010, pp. 155-159, vol. 11, No. 3.
Holtzman et al., "Nerve Growth Factor Protects the Neonatal Brain Against Hypoxic-Ischemic Injury", Annals of Neurology, 1996, pp. 114-122, vol. 39, No. 1.
International Search Report and Written Opinion from related International Application No. PCT/US2013/049333, dated Oct. 14, 2013; 17 pgs.
Kfoury et al., "Trans-cellular Propagation of Tau Aggregation by Fibrillar Species", Journal of Biological Chemistry, 2012, pp. 19440-19451, vol. 287, No. 23.

(Continued)

*Primary Examiner* — Adam Weidner
(74) *Attorney, Agent, or Firm* — Dechert LLP

(57) ABSTRACT

Provided herein is an isolated antibody or antigen-binding fragment that specifically binds tau, the antibody or fragment comprising a heavy chain variable (VH) region and a light chain variable (VL) region having amino acid sequences set forth herein. Also provided are methods of preventing or treating a tauopathy in a subject, comprising administering to a human in need of therapy for a tauopathy with one or more antibodies or fragments as described herein, wherein the antibodies or antigen-binding fragment are administered under conditions and in an amount effective to prevent or treat the tauopathy.

12 Claims, 17 Drawing Sheets

(56) References Cited

U.S. PATENT DOCUMENTS

| | | |
|---|---|---|
| 2011/0177109 A1 | 7/2011 | Smith, III et al. |
| 2011/0250213 A1* | 10/2011 | Tso .................. C07K 16/2866 424/174.1 |
| 2011/0271358 A1* | 11/2011 | Freeman ............ C07K 16/2818 800/13 |
| 2011/0305706 A1 | 12/2011 | Brady et al. |
| 2011/0318358 A1 | 12/2011 | Sigurdsson et al. |
| 2012/0087861 A1 | 4/2012 | Nitsch et al. |
| 2012/0142602 A1 | 6/2012 | Brady et al. |
| 2012/0183599 A1 | 7/2012 | Pfeifer et al. |
| 2012/0276009 A1 | 11/2012 | Pfeifer et al. |
| 2012/0302595 A1 | 11/2012 | Baulieu et al. |
| 2012/0321594 A1 | 12/2012 | Hong et al. |
| 2013/0022544 A1 | 1/2013 | Wisniewski |
| 2013/0028914 A1 | 1/2013 | Kayed |
| 2013/0095492 A1 | 4/2013 | DeBernardis et al. |
| 2014/0056901 A1 | 2/2014 | Agadjanyan et al. |
| 2014/0159244 A1 | 6/2014 | Lu et al. |
| 2014/0161875 A1 | 6/2014 | Winderickx et al. |
| 2014/0171373 A1 | 6/2014 | Karen et al. |
| 2014/0286954 A1 | 9/2014 | Moe et al. |
| 2014/0294724 A1 | 10/2014 | Chain |
| 2014/0294731 A1 | 10/2014 | Pfeifer et al. |
| 2014/0302046 A1 | 10/2014 | Sigurdsson |
| 2015/0050215 A1 | 2/2015 | Novak et al. |
| 2015/0064726 A1 | 3/2015 | Michaelsen et al. |
| 2015/0175682 A1 | 6/2015 | Pfeifer et al. |
| 2015/0183854 A1 | 7/2015 | Mod et al. |
| 2015/0183855 A1 | 7/2015 | Diamond et al. |
| 2015/0232524 A1 | 8/2015 | Agadjanyan et al. |
| 2015/0232544 A1 | 8/2015 | Griswold-Prenner et al. |
| 2015/0259406 A1 | 9/2015 | Pfeifer et al. |
| 2015/0266947 A1 | 9/2015 | Sierks et al. |
| 2015/0307600 A1 | 10/2015 | Alderfer et al. |
| 2015/0309054 A1 | 10/2015 | Diamond et al. |
| 2015/0344553 A1 | 12/2015 | Weinreb et al. |
| 2016/0024193 A1 | 1/2016 | Ayalon et al. |
| 2016/0031976 A1 | 2/2016 | Seubert et al. |
| 2016/0031977 A1 | 2/2016 | Lu et al. |

FOREIGN PATENT DOCUMENTS

| | | |
|---|---|---|
| EP | 0310132 A2 | 4/1989 |
| ES | 2321996 L | 6/2009 |
| WO | 9311231 A1 | 6/1993 |
| WO | 9418560 A1 | 8/1994 |
| WO | 9822120 A1 | 5/1998 |
| WO | 200014546 A1 | 10/2000 |
| WO | 2012045882 A2 | 4/2012 |
| WO | 2012106363 A2 | 8/2012 |
| WO | 2013177104 A2 | 11/2013 |
| WO | 2014008404 A1 | 1/2014 |
| WO | 201496321 A1 | 6/2014 |
| WO | 2014159244 A2 | 10/2014 |
| WO | 2015200806 A2 | 12/2015 |

OTHER PUBLICATIONS

Khuchua et al., "Deletion of the N-Terminus of Murine MAP2 by Gene Targeting Disrupts Hippocampal CA1 Neuron Architecture and Alters Contextual Memory", Neuroscience, 2003, pp. 101-111, vol. 119, No. 1.

LoPresti et al., "Functional implications for the microtubule-associated protein tau: Localization in oligodendrocytes", Proc. Natl. Acad. Sci. USA, 1995, pp. 10369-10373, vol. 92, No. 22.

Porzig et al., "Epitope mapping of mAbs AT8 and Tau5 directed against hyperphosphorylated regions of the human tau protein", Biochemical and Biophysical Research Communications, 2007, pp. 644-649, vol. 358, No. 2.

Troquier et al., "Targeting Phospho-Ser422 by Active Tau Immunotherapy in the THY-Tau22 Mouse Model: A Suitable Therapeutic Approach", Current Alzheimer Research, 2012, pp. 397-405, vol. 9.

Wozniak et al., "Apoptotic neurodegeneration induced by ethanol in neonatal mice is associated with profound learning/memory deficits in juveniles followed by progressive functional recovery in adults", Neurobiology of Disease, 2004, pp. 403-414, vol. 17, No. 3.

Yamada_et_al., "In Vivo Microdialysis Reveals Age-Dependent Decrease of Brain Interstitial Fluid Tau Levels in P301S Human Tau Transgenic Mice", The Journal of Neuroscience, 2011, pp. 13110-13117, vol. 31, No. 37.

Yanamandra_et_al., "Anti-tau antibodies that block tau aggregate seeding in vitro markedly decrease pathology and improve cognition in vivo", NIH Public Access, 2013, pp. 402-414, vol. 80, No. 2.

Intellectual Property Office of Singapore Search Report and Written Opinion from related International Application No. 11201408626Y, dated Apr. 20, 2016; 10 pgs.

Supplemental European Search Report for Application No. 13813988.6 dated Jun. 5, 2016.

Slide_Presentation_Aug 6, 2013.

* cited by examiner

C2N Grafted V Region Sequences

Light Chain

|  | CDR1 | CDR2 | CDR3 |
|---|---|---|---|
| MuVL | DIVLTQSPASLAVSLGQRATISCRASQSVSTSRYSYIHWYQQKPGQPPKLLIKYASNLESGVPARFSGSGSGTDFTLNIHPLEEEDAATYYCHHSWEIPLTFGAGTKLELK (SEQ ID NO:11) |
| VK1 | DIVLTQSPDSLAVSLGERATISCRASQSVSTSRYSYIHWYQQKPGQPPKLLIKYASNLESGVPSRFSGSGSGTDPTLNIHPLREEDFATYYCHHSWEIPLTFGQGTKLEIK (6) (SEQ ID NO:1) |
| VK2 | DIVLTQSPDSLAVSLGERATISCRASQSVSTSRYSYIHWYQQKPGQFPKLLIKYASNLESGVPSRFSGSGSGTDFTLNIHPLEEDFATYYCHHSWEIPLTFGQGTKLEIK (7) (SEQ ID NO:2) |
| VK3 | DIVLTQSPDSLAVSLGERATISCRASQSVSTSRYSYIHWYQQKPGQPPKLLIKYASNLESGVPSRFSGSGSGTDFTLTISSLQPEDFATYYCHHSWEIPLTFGQGTKLEIK (11) (SEQ ID NO:3) |
| VK4 | DIVLMQSPDSLAVSLGERATISCRASQSVSTSRYSYIHWYQQKPGQPPKLLIKYASNLESGVPSRFSGSGSGTDFTLTISSLQPEDFATYYCHHSWEIPLTFGQGTKLEIK (12) (SEQ ID NO:4) |

Heavy Chain

|  | CDR1 | CDR2 | CDR3 |
|---|---|---|---|
| MuVH | EVKVVEESGGGLVQPGGSMKLSCVVSGFTFSNYWMNWVRQSPEKGLEWVAQIRLKSDNYATHYEESVKGRFTISRDDSKSSVYLQMNNLRAEDSGIYYCTNWEDYWGQGTTLTVSSASTKGPSVF (SEQ ID NO:12) |
| VH1 | EVKVVESGGGLVQPGGSMKLSCVVSGFTFSNYWMNWVRQAPGKGLEWVAQIRLKSDNYATHYEESVKGRFTISRDDSKSSVYLQMNNLRAEDSGIYYCTNWEDYWGQGTTVTVSSASTKGPSVF (SEQ ID NO:5) |
| VH2 | EVKVVESGGGLVQPGGSIKLSCVVSGFTFSNYWMNWVRQAPGKGLEWVAQIRLKSDNYATHYEESVKGRFTISRDDSKSSVYLQMNSLRAEDTGIYYCTNWEDYWGQGTTVTVSSASTKGPSVF (SEQ ID NO:6) |
| VH3 | EVQVVESGGGLVQPGGSIKLSCVVSGFTFSNYWMNWVRQAPGKGLEWVAQIRLKSDNYATHYEESVKGRFTISRDDSKMSVYLQMNSLRAEDTAIYYCTNWEDYWGQGTTVTVSSASTKGPSVF (SEQ ID NO:7) |
| VH4 | EVQLVESGGGLVQPGGSLKLSCVVSGFTFSNYWMNWVRQAPGKGLEWVAQIRLKSDNYATHYEESVKGRFTISRDDSKNSLYLQMNSLRAEDTAIYYCTNWEDYWGQGTTVTVSSASTKGPSVF (SEQ ID NO:8) |

Key:
Mu: Denotes the murine sequence
VH: Denotes the humanized variable heavy chain
VL: Denotes the humanized variable light chain
CDR: Complementary determining region

*FIG. 1*

Full Amino Acid Sequences of C$_2$N Heavy Chain and Light Chain Variants
Grafted Heavy Chain Variants gVH1 Theoretical pI/Mw: 6.80 / 48822.90

EVKVVESGGGLVQPGGSMKLSCVVSGFTFSNYWVNWVRQAPGKGLEWVAQIRLKSDNYATHYEESVKG
RFTISRDDSKSSVYLQMNNLRAEDSGIYYCTNWEDYWGQGTTVTVSSASTKGPSVFPLAPCSRSTSES
TAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK (SEQ ID NO:13)

*FIG. 2A*

Full Amino Acid Sequences of C$_2$N Heavy Chain and Light Chain Variants
Grafted Heavy Chain Variants gVH2 Theoretical pI/Mw: 6.80 / 48791.87

EVKVVESGGGLVQPGGSLKLSCVVSGFTFSNYWVNWVRQAPGKGLEWVAQIRLKSDNYATHYEESVKG
RFTISRDDSKSSVYLQMNSLRAEDTGIYYCTNWEDYWGQGTTVTVSSASTKGPSVFPLAPCSRSTSES
TAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK (SEQ ID NO:14)

*FIG. 2B*

Full Amino Acid Sequences of C$_2$N Heavy Chain and Light Chain Variants
Grafted Heavy Chain Variants gVH3 Theoretical pI/Mw: 6.51 / 48832.88

EVQVVESGGGLVQPGGSLKLSCVVSGFTFSNYWVNWVRQAPGKGLEWVAQIRLKSDNYATHYEESVKG
RFTISRDDSKNSVYLQMNSLRAEDTAIYYCTNWEDYWGQGTTVTVSSASTKGPSVFPLAPCSRSTSES
TAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK (SEQ ID NO:15)

*FIG. 2C*

Full Amino Acid Sequences of C$_2$N Heavy Chain and Light Chain Variants
Grafted Heavy Chain Variants gVH4 Theoretical pI/Mw: 6.51 / 48860.93

EVQLVESGGGLVQPGGSLKLSCVVSGFTFSNYWVNWVRQAPGKGLEWVAQIRLKSDNYATHYEESVKG
RFTISRDDSKNSLYLQMNSLRAEDTAIYYCTNWEDYWGQGTTVTVSSASTKGPSVFPLAPCSRSTSES
TAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTPPVLDSDGSFFLYSRLTVD
KSRWQEGNVFSCSVMHEALHNHYTQKSLSLSLGK (SEQ ID NO:16)

*FIG. 2D*

Full Amino Acid Sequences of C₂N Heavy Chain and Light Chain Variants
Grafted Light Chain Variants gVL1 Theoretical pI/Mw: 6.08 / 24100.81

DIVLTQSPDSLAVSLGERATISCRASQSVSTSRYSYIHWYQQKPGQPPKLLIKYASNLESGVPSRFSG
SGSGTDFTLNIHPLEEEDFATYYCHHSWEIPLTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQG
LSSPVTKSFNRGEC (SEQ ID NO:17)

*FIG. 2E*

Full Amino Acid Sequences of C₂N Heavy Chain and Light Chain Variants
Grafted Light Chain Variants gVL2 Theoretical pI/Mw: 6.33 / 24068.81

DIVLTQSPDSLAVSLGERATISCRASQSVSTSRYSYIHWYQQKPGQPPKLLIKYASNLESGVPSRFSG
SGSGTDFTLNIHPLEPEDFATYYCHHSWEIPLTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQG
LSSPVTKSFNRGEC (SEQ ID NO:18)

*FIG. 2F*

Full Amino Acid Sequences of C₂N Heavy Chain and Light Chain Variants
Grafted Light Chain Variants gVL3 Theoretical pI/Mw: 6.57 / 23994.72

DIVLTQSPDSLAVSLGERATISCRASQSVSTSRYSYIHWYQQKPGQPPKLLIKYASNLESGVPSRFSG
SGSGTDFTLTISSLQPEDFATYYCHHSWEIPLTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQG
LSSPVTKSFNRGEC (SEQ ID NO:19)

*FIG. 2G*

Full Amino Acid Sequences of C₂N Heavy Chain and Light Chain Variants
Grafted Light Chain Variants gVL4 Theoretical pI/Mw: 6.57 / 24012.76

DIVLTQSPDSLAVSLGERATISCRASQSVSTSRYSYIHWYQQKPGQPPKLLIKYASNLESGVPSRFSG
SGSGTDFTLTISSLQPEDFATYYCHHSWEIPLTFGQGTKLEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQG
LSSPVTKSFNRGEC (SEQ ID NO:20)

*FIG. 2H*

Transient Expression Data From Humanized Variants

| Humanized Variant | Transient Expression Round 1 (µg/mL) | Transient Expression Round 2 (µg/mL) |
|---|---|---|
| VH1/VK1 | 9.0 | |
| VH1/VK2 | 13.4 | 13.1 |
| VH1/VK3 | 22.2 | 20.2 |
| VH1/VK4 | 12.4 | |
| VH2/VK1 | 6.5 | |
| VH2/VK2 | 11.3 | 6.2 |
| VH2/VK3 | 13.7 | 13.8 |
| VH2/VK4 | 9.3 | |
| VH3/VK1 | 7.3 | |
| VH3/VK2 | 12.0 | 8.1 |
| VH3/VK3 | 15.2 | 15.9 |
| VH3/VK4 | 6.4 | |
| VH4/VK3 | 3.6 | |

*FIG. 3*

Potency Assay

| Antibody | IC50 (Relative to Chimera) | | |
|---|---|---|---|
| | C$_2$N Run 1 | C$_2$N Run 2 | External |
| Chimera | 1.00 | 1.00 | 1.00 |
| VH1/VK1 | 1.49 | 1.11 | 0.84 |
| VH1/VK2 | 1.34 | 0.91 | 0.78 |
| VH1/VK3.1 | 1.58 | 0.92 | 0.79 |
| VH1/VK3.2 | 1.93 | 1.07 | 1.02 |
| VH1/VK4 | 2.05 | 1.02 | 1.41 |
| VH2/VK1 | 1.43 | 1.02 | 1.02 |
| VH2/VK2 | 1.37 | 0.85 | 1.12 |
| VH2/VK3 | 1.17 | 0.97 | 0.94 |
| VH2/VK4 | 1.36 | 1.03 | 1.37 |
| VH3/VK1 | 1.16 | 1.42 | 1.04 |
| VH3/VK2 | 0.81 | 1.28 | 0.94 |
| VH3/VK3 | 0.84 | 1.34 | 0.93 |
| VH3/VK4 | 0.89 | 1.22 | 1.51 |
| VH4/VK3 | 1.79 | 1.9 | 1.31 |
| HJ8.5 | 0.79 | 0.99 | 1.07 |

*FIG. 4*

Antibody Binding Kinetics Against Human Tau

| Humanized Variant | Association Constant $K_a$ (1/Ms) | Dissociation Constant $K_d$ (1/s) | Affinity $K_D$ (M) |
|---|---|---|---|
| Chimera | 7.21E+05 | 1.43E-03 | 1.99E-09 |
| VH1/VK2 | 3.02E+05 | 6.21E-04 | 2.06E-09 |
| VH1/VK4 | 2.87E+05 | 5.99E-04 | 2.09E-09 |
| VH2/VK3 | 2.73E+05 | 6.08E-04 | 2.23E-09 |
| VH2/VK4 | 2.80E+05 | 5.93E-04 | 2.13E-09 |
| VH3/VK3 | 2.76E+05 | 5.15E-04 | 1.88E-09 |
| VH3/VK4 | 2.65E+05 | 5.07E-04 | 1.92E-09 |

*FIG. 5*

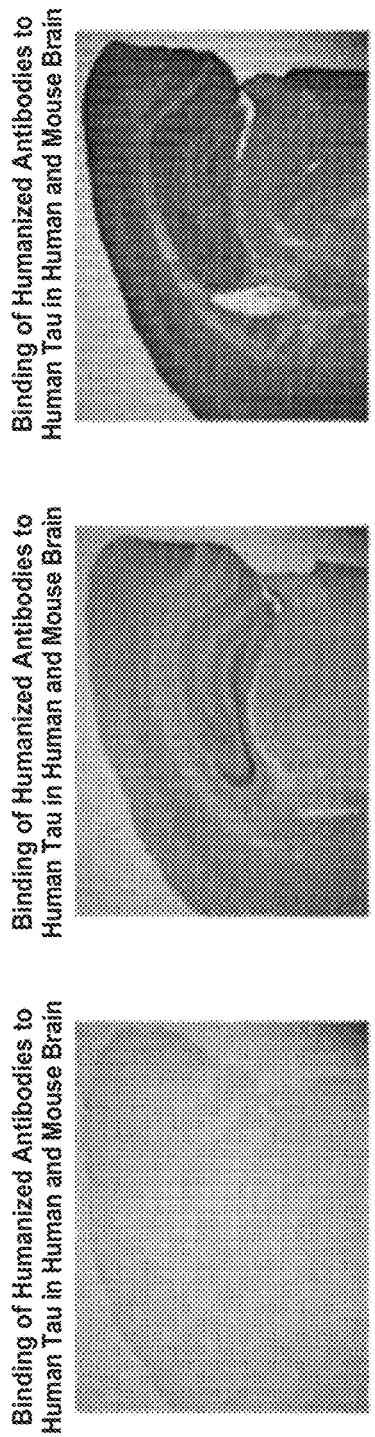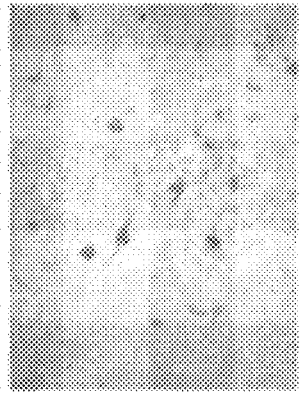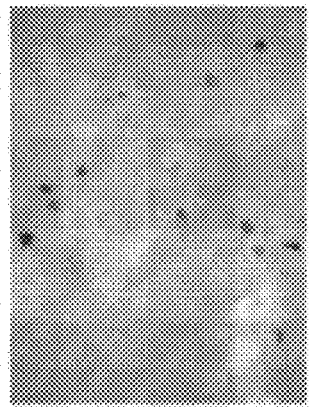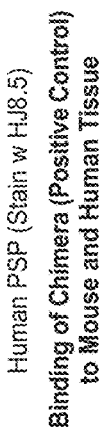
FIG. 7A FIG. 7B FIG. 7C FIG. 7D FIG. 7E

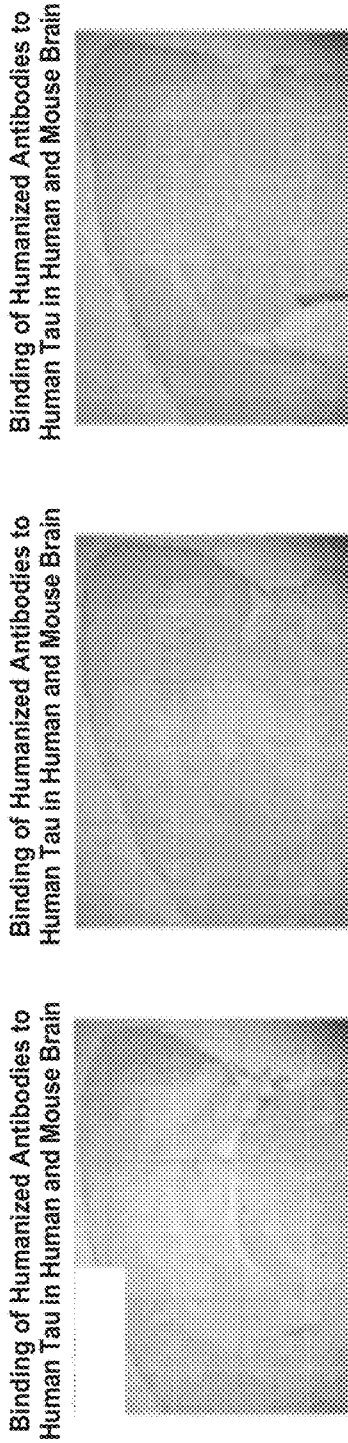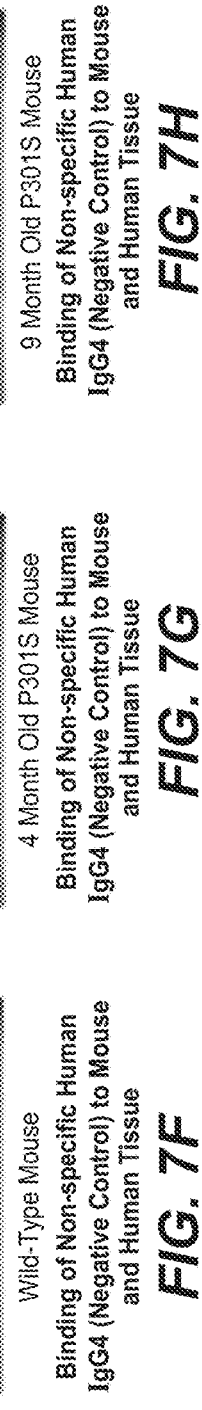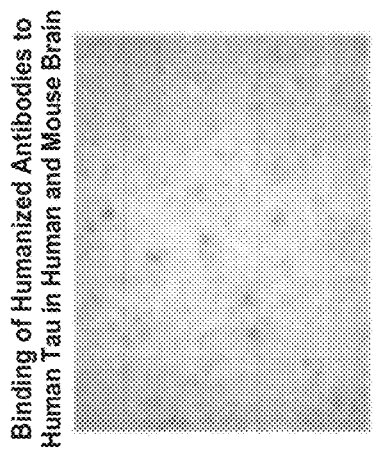

Binding of Humanized Antibodies to Human Tau in Human and Mouse Brain

Wild-Type Mouse
Binding of Non-specific Human IgG4 (Negative Control) to Mouse and Human Tissue

FIG. 7F

Binding of Humanized Antibodies to Human Tau in Human and Mouse Brain

4 Month Old P301S Mouse
Binding of Non-specific Human IgG4 (Negative Control) to Mouse and Human Tissue

FIG. 7G

Binding of Humanized Antibodies to Human Tau in Human and Mouse Brain

9 Month Old P301S Mouse
Binding of Non-specific Human IgG4 (Negative Control) to Mouse and Human Tissue

FIG. 7H

Binding of Humanized Antibodies to Human Tau in Human and Mouse Brain

Human AD Cortex Tissue #2
Binding of Non-specific Human IgG4 (Negative Control) to Mouse and Human Tissue

FIG. 7I

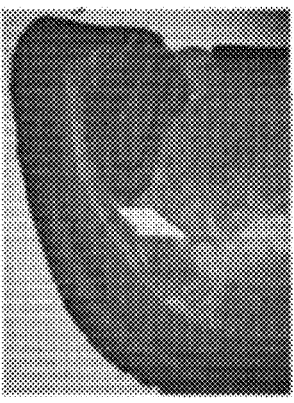

FIG. 7J
Wild-Type Mouse
Binding of VH1/VK2 to Mouse and Human Tissue
Binding of Humanized Antibodies to Human Tau in Human and Mouse Brain

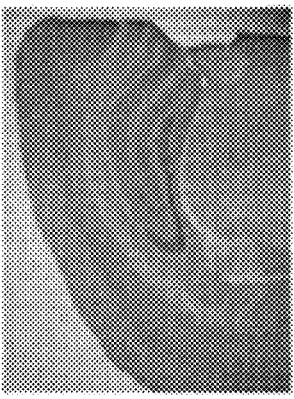

FIG. 7K
4 Month Old P301S Mouse
Binding of VH1/VK2 to Mouse and Human Tissue
Binding of Humanized Antibodies to Human Tau in Human and Mouse Brain

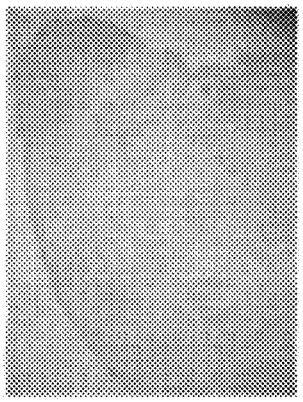

FIG. 7L
9 Month Old P301S Mouse
Binding of VH1/VK2 to Mouse and Human Tissue
Binding of Humanized Antibodies to Human Tau in Human and Mouse Brain

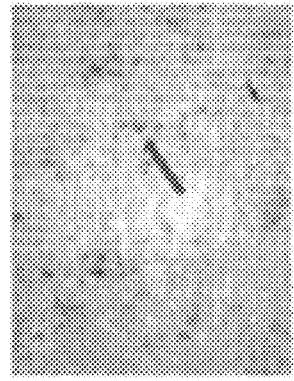

FIG. 7M
Human PSP
Binding of VH1/VK2 to Mouse and Human Tissue
Binding of Humanized Antibodies to Human Tau in Human and Mouse Brain

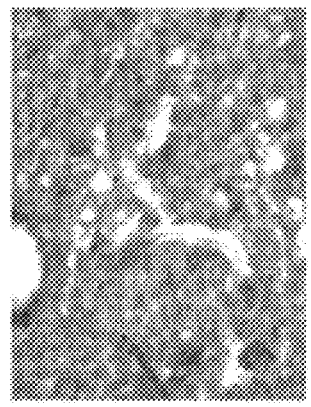

FIG. 7N
Human AD Cortex Tissue #2
Binding of VH1/VK2 to Mouse and Human Tissue
Binding of Humanized Antibodies to Human Tau in Human and Mouse Brain

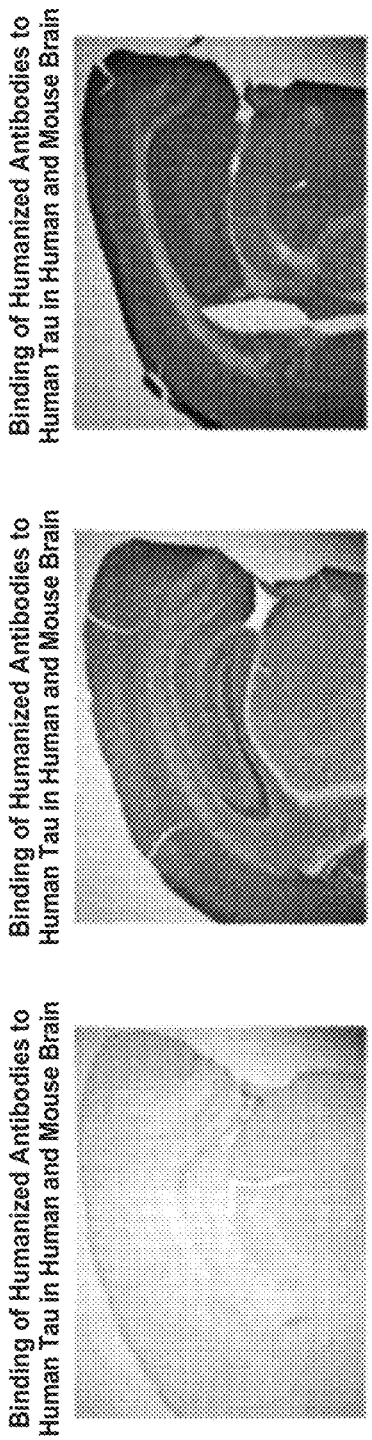

FIG. 7O — Wild-Type Mouse, Binding of VH1/VK3 to Mouse and Human Tissue. Binding of Humanized Antibodies to Human Tau in Human and Mouse Brain FIG. 7P — 4 Month Old P301S Mouse, Binding of VH1/VK3 to Mouse and Human Tissue. Binding of Humanized Antibodies to Human Tau in Human and Mouse Brain FIG. 7Q — 9 Month Old P301S Mouse, Binding of VH1/VK3 to Mouse and Human Tissue. Binding of Humanized Antibodies to Human Tau in Human and Mouse Brain FIG. 7R — Human PSP, Binding of VH1/VK3 to Mouse and Human Tissue. Binding of Humanized Antibodies to Human Tau in Human and Mouse Brain FIG. 7S — Human AD Cortex Tissue #2, Binding of VH1/VK3 to Mouse and Human Tissue. Binding of Humanized Antibodies to Human Tau in Human and Mouse Brain

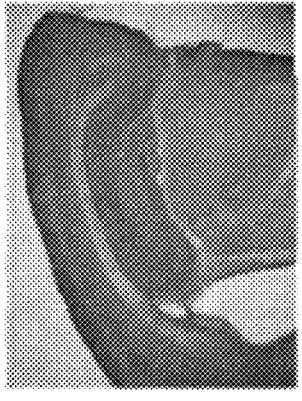

Binding of Humanized Antibodies to
Human Tau in Human and Mouse Brain

Wild-Type Mouse
Binding of VH2/VK2 to Mouse
and Human Tissue

FIG. 7T

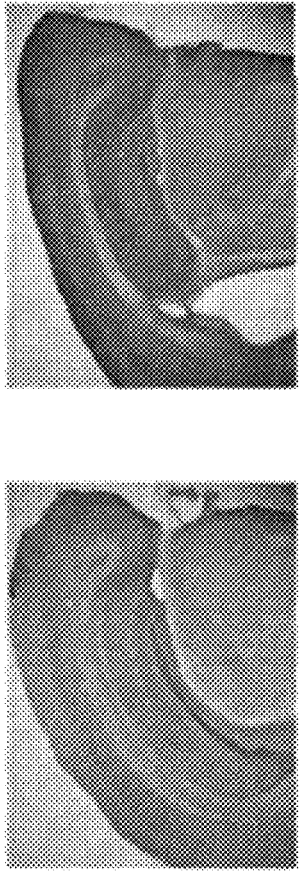

Binding of Humanized Antibodies to
Human Tau in Human and Mouse Brain

4 Month Old P301S Mouse
Binding of VH2/VK2 to Mouse
and Human Tissue

FIG. 7U

Binding of Humanized Antibodies to
Human Tau in Human and Mouse Brain

9 Month Old P301S Mouse
Binding of VH2/VK2 to Mouse
and Human Tissue

FIG. 7V

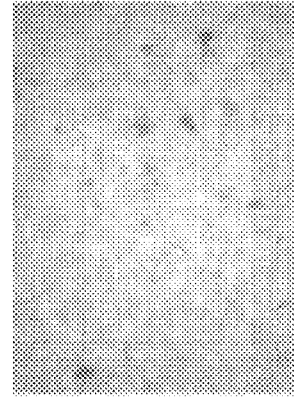

Binding of Humanized Antibodies to
Human Tau in Human and Mouse Brain

Human AD Cortex Tissue #2
Binding of VH2/VK2 to Mouse
and Human Tissue

FIG. 7X

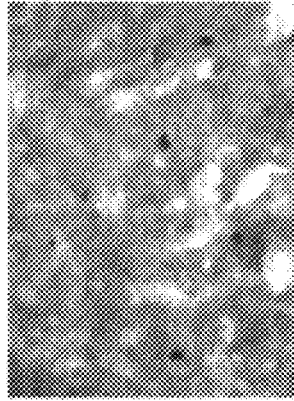

Human PSP
Binding of VH2/VK2 to Mouse
and Human Tissue

FIG. 7W

Binding of Humanized Antibodies to
Human Tau in Human and Mouse Brain

Wild-Type Mouse
Binding of VH2/VK3 to Mouse
and Human Tissue

FIG. 7Y

Binding of Humanized Antibodies to
Human Tau in Human and Mouse Brain

4 Month Old P301S Mouse
Binding of VH2/VK3 to Mouse
and Human Tissue

FIG. 7Z

Binding of Humanized Antibodies to
Human Tau in Human and Mouse Brain

9 Month Old P301S Mouse
Binding of VH2/VK3 to Mouse
and Human Tissue

FIG. 7AA

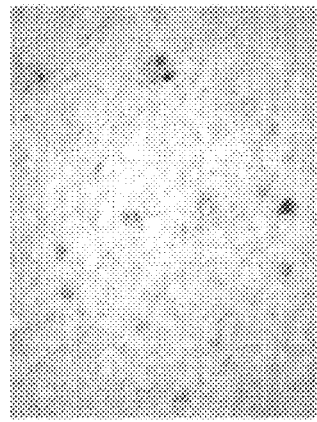

Binding of Humanized Antibodies to
Human Tau in Human and Mouse Brain

Human AD Cortex Tissue #2
Binding of VH2/VK3 to Mouse
and Human Tissue

FIG. 7CC

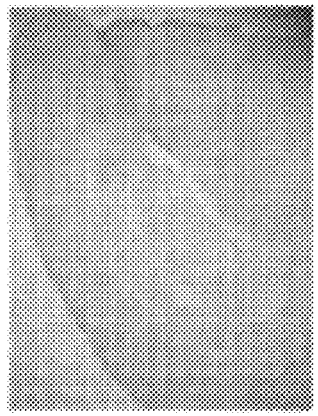

Binding of Humanized Antibodies to
Human Tau in Human and Mouse Brain

Human PSP
Binding of VH2/VK3 to Mouse
and Human Tissue

FIG. 7BB

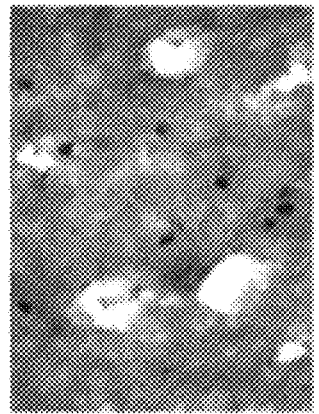

Wild-Type Mouse
Binding of VH3/VK2 to Mouse and Human Tissue

4 Month Old P301S Mouse
Binding of VH3/VK2 to Mouse and Human Tissue

9 Month Old P301S Mouse
Binding of VH3/VK2 to Mouse and Human Tissue

Human PSP
Binding of VH3/VK2 to Mouse and Human Tissue

Human AD Cortex Tissue #2
Binding of VH3/VK2 to Mouse and Human Tissue

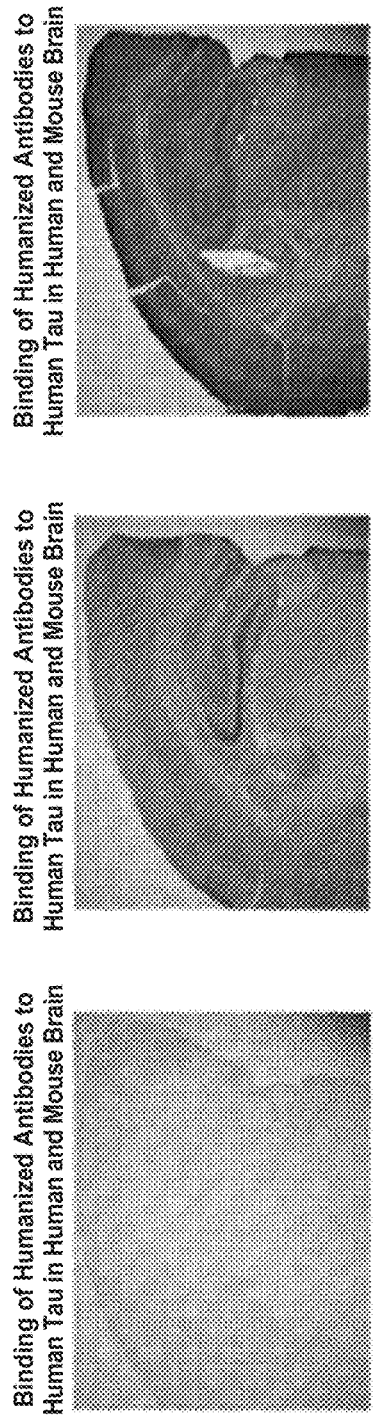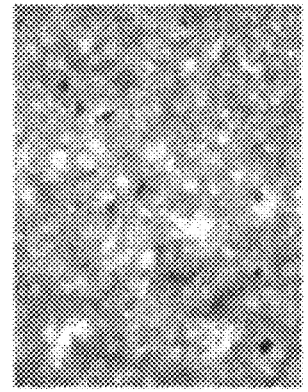
FIG. 7II — Wild-Type Mouse — Binding of VH3/VK3 to Mouse and Human Tissue
FIG. 7JJ — 4 Month Old P301S Mouse — Binding of VH3/VK3 to Mouse and Human Tissue
FIG. 7KK — 9 Month Old P301S Mouse — Binding of VH3/VK3 to Mouse and Human Tissue
FIG. 7LL — Human PSP — Binding of VH3/VK3 to Mouse and Human Tissue
FIG. 7MM — Human AD Cortex Tissue #2 — Binding of VH3/VK3 to Mouse and Human Tissue Epitope Mapping of C$_2$N-8E12 and HJ8.5

| Antibodies | Core Epitopes |
|---|---|
| HJ8.5 and C$_2$N-8E12 | $_{25}$DQGGYT$_{30}$ (SEQ ID NO:9) |

| PepLabData | SEQUENCE | Identifier | Label | HJ8.5 (Binding Signal) | C$_2$N-8E12 (Binding Signal) |
|---|---|---|---|---|---|
| PEP_2875800 | DHAGTYGLGDRKDQG | SEQ ID NO:24 | LIN | 61 | 78 |
| PEP_2875801 | DHAGTYGLGAAKDQG | SEQ ID NO:25 | LIN.AA | 52 | 90 |
| PEP_2875802 | HAGTYGLGDRKDQGG | SEQ ID NO:26 | LIN | 63 | 65 |
| PEP_2875803 | HAGTYGLGDAADQGG | SEQ ID NO:27 | LIN.AA | 51 | 65 |
| PEP_2875804 | AGTYGLGDRKDQGGY | SEQ ID NO:28 | LIN | 427 | 1286 |
| PEP_2875805 | AGTYGLGDRAAQGGY | SEQ ID NO:29 | LIN.AA | 58 | 76 |
| PEP_2875806 | GTYGLGDRKDQGGYT | SEQ ID NO:30 | LIN | 2638 | 1714 |
| PEP_2875807 | GTYGLGDRKAAGGYT | SEQ ID NO:31 | LIN.AA | 110 | 114 |
| PEP_2875808 | TYGLGDRKDQGGYTM | SEQ ID NO:32 | LIN | 2640 | 2588 |
| PEP_2875809 | TYGLGDRKDAAGYTM | SEQ ID NO:33 | LIN.AA | 2814 | 2755 |
| PEP_2875810 | YGLGDRKDQGGYTMH | SEQ ID NO:34 | LIN | 2844 | 2671 |
| PEP_2875811 | YGLGDRKDQAAYTMH | SEQ ID NO:35 | LIN.AA | 1780 | 1876 |
| PEP_2875812 | GLGDRKDQGGYTMHQ | SEQ ID NO:36 | LIN | 2824 | 2729 |
| PEP_2875813 | GLGDRKDQGAATMHQ | SEQ ID NO:37 | LIN.AA | 80 | 65 |
| PEP_2875814 | LGDRKDQGGYTMHQD | SEQ ID NO:38 | LIN | 2835 | 2749 |
| PEP_2875815 | LGDRKDQGGAAMHQD | SEQ ID NO:39 | LIN.AA | 69 | 99 |
| PEP_2875816 | GDRKDQGGYTMHQDQ | SEQ ID NO:40 | LIN | 2647 | 2699 |
| PEP_2875817 | GDRKDQGGYAAHQDQ | SEQ ID NO:41 | LIN.AA | 2635 | 661 |
| PEP_2875818 | DRKDQGGYTMHQDQE | SEQ ID NO:42 | LIN | 2692 | 2788 |
| PEP_2875819 | DRKDQGGYTAAQDQE | SEQ ID NO:43 | LIN.AA | 2697 | 2585 |
| PEP_2875820 | RKDQGGYTMHQDQEG | SEQ ID NO:44 | LIN | 2699 | 2779 |
| PEP_2875821 | RKDQGGYTMAADQEG | SEQ ID NO:45 | LIN.AA | 2713 | 2791 |
| PEP_2875822 | KDQGGYTMHQDQEGD | SEQ ID NO:46 | LIN | 2701 | 2680 |
| PEP_2875823 | KDQGGYTMHAAQEGD | SEQ ID NO:47 | LIN.AA | 2707 | 2712 |
| PEP_2875824 | DQGGYTMHQDQEGDT | SEQ ID NO:48 | LIN | 2677 | 2648 |
| PEP_2875825 | DQGGYTMHQAAEGDT | SEQ ID NO:49 | LIN.AA | 2707 | 2585 |
| PEP_2875826 | QGGYTMHQDQEGDTD | SEQ ID NO:50 | LIN | 399 | 789 |
| PEP_2875827 | QGGYTMHQDAAGDTD | SEQ ID NO:51 | LIN.AA | 427 | 636 |
| PEP_2875828 | GGYTMHQDQEGDTDA | SEQ ID NO:52 | LIN | 109 | 110 |
| PEP_2875829 | GGYTMHQDQAADTDA | SEQ ID NO:53 | LIN.AA | 106 | 118 |
| PEP_2875830 | GYTMHQDQEGDTDAG | SEQ ID NO:54 | LIN | 77 | 97 |

*FIG. 9*

SEQUENCE LISTING

```
<160> NUMBER OF SEQ ID NOS: 55

<210> SEQ ID NO 1
<211> LENGTH: 111
<212> TYPE: PRT
<213> ORGANISM: Homo sapiens

<400> SEQUENCE: 1

Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Asn Ile His
65                  70                  75                  80

Pro Leu Glu Glu Glu Asp Phe Ala Thr Tyr Tyr Cys His His Ser Trp
                85                  90                  95

Glu Ile Pro Leu Thr Phe Gly Gln Gly Thr Lys Leu Glu Ile Lys
            100                 105                 110

<210> SEQ ID NO 2
<211> LENGTH: 111
<212> TYPE: PRT
<213> ORGANISM: Homo sapiens

<400> SEQUENCE: 2

Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60
```

Arg Phe Ser Gly Ser Gly Ser Gly Thr Asp Phe Thr Leu Asn Ile His
65                  70                  75                  80

Pro Leu Glu Pro Glu Asp Phe Ala Thr Tyr Tyr Cys His His Ser Trp
                85                  90                  95

Glu Ile Pro Leu Thr Phe Gly Gln Gly Thr Lys Leu Glu Ile Lys
            100                 105                 110

<210> SEQ ID NO 3
<211> LENGTH: 111
<212> TYPE: PRT
<213> ORGANISM: Homo sapiens

<400> SEQUENCE: 3

Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His His Ser Trp
                85                  90                  95

Glu Ile Pro Leu Thr Phe Gly Gln Gly Thr Lys Leu Glu Ile Lys
            100                 105                 110

<210> SEQ ID NO 4
<211> LENGTH: 111
<212> TYPE: PRT
<213> ORGANISM: Homo sapiens

<400> SEQUENCE: 4

Asp Ile Val Leu Met Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His His Ser Trp
                85                  90                  95

Glu Ile Pro Leu Thr Phe Gly Gln Gly Thr Lys Leu Glu Ile Lys
            100                 105                 110

<210> SEQ ID NO 5
<211> LENGTH: 124
<212> TYPE: PRT
<213> ORGANISM: Homo sapiens

<400> SEQUENCE: 5

Glu Val Lys Val Val Glu Ser Gly Gly Gly Leu Val Gln Pro Gly Gly
1               5                   10                  15

Ser Met Lys Leu Ser Cys Val Val Ser Gly Phe Thr Phe Ser Asn Tyr

```
                    20                  25                  30

Trp Val Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Ser Gly Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe
        115                 120
```

<210> SEQ ID NO 6
<211> LENGTH: 124
<212> TYPE: PRT
<213> ORGANISM: Homo sapiens

<400> SEQUENCE: 6

```
Glu Val Lys Val Val Glu Ser Gly Gly Gly Leu Val Gln Pro Gly Gly
1               5                   10                  15

Ser Leu Lys Leu Ser Cys Val Val Ser Gly Phe Thr Phe Ser Asn Tyr
            20                  25                  30

Trp Val Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe
        115                 120
```

<210> SEQ ID NO 7
<211> LENGTH: 124
<212> TYPE: PRT
<213> ORGANISM: Homo sapiens

<400> SEQUENCE: 7

```
Glu Val Gln Val Val Glu Ser Gly Gly Gly Leu Val Gln Pro Gly Gly
1               5                   10                  15

Ser Leu Lys Leu Ser Cys Val Val Ser Gly Phe Thr Phe Ser Asn Tyr
            20                  25                  30

Trp Val Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Asn Ser
65                  70                  75                  80

Val Tyr Leu Gln Met Asn Ser Leu Arg Ala Glu Asp Thr Ala Ile Tyr
                85                  90                  95

Tyr Cys Thr Asn Trp Glu Asp Tyr Trp Gly Gln Gly Thr Thr Val Thr
```

```
                    100                 105                 110
Val Ser Ser Ala Ser Thr Lys Gly Pro Ser Val Phe
            115                 120

<210> SEQ ID NO 8
<211> LENGTH: 124
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Val Val Ser Gly Phe Thr Phe Ser Asn Tyr
            20                  25                  30

Trp Val Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Glu Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe
            115                 120

<210> SEQ ID NO 9
<211> LENGTH: 6
<212> TYPE: PRT
<213> ORGANISM: Homo sapiens

<400> SEQUENCE: 9

Asp Gln Gly Gly Tyr Thr
1               5

<210> SEQ ID NO 10
<211> LENGTH: 8
<212> TYPE: PRT
<213> ORGANISM: Homo sapiens

<400> SEQUENCE: 10

Gly Tyr Thr Met His Gln Asp Gln
1               5

<210> SEQ ID NO 11
<211> LENGTH: 111
<212> TYPE: PRT
<213> ORGANISM: Homo sapiens

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60
```

Arg Phe Ser Gly Ser Gly Ser Gly Thr Asp Phe Thr Leu Asn Ile His
65                  70                  75                  80

Pro Leu Glu Glu Glu Asp Ala Ala Thr Tyr Tyr Cys His His Ser Trp
                85                  90                  95

Glu Ile Pro Leu Thr Phe Gly Ala Gly Thr Lys Leu Glu Leu Lys
            100                 105                 110

<210> SEQ ID NO 12
<211> LENGTH: 124
<212> TYPE: PRT
<213> ORGANISM: Homo sapiens

<400> SEQUENCE: 12

Glu Val Lys Val Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Val Asn Trp Val Arg Gln Ser Pro Glu Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Ser Gly Ile Tyr
                85                  90                  95

Tyr Cys Thr Asn Trp Glu Asp Tyr Trp Gly Gln Gly Thr Thr Leu Thr
            100                 105                 110

Val Ser Ser Ala Ser Thr Lys Gly Pro Ser Val Phe
        115                 120

<210> SEQ ID NO 13
<211> LENGTH: 442
<212> TYPE: PRT
<213> ORGANISM: Homo sapiens

<400> SEQUENCE: 13

Glu Val Lys Val Val Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Val Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Ser Gly Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

-continued

Leu Thr Ser Gly Val His Thr Phe Pro Ala Val Leu Gln Ser Ser Gly
165                 170                 175

Leu Tyr Ser Leu Ser Ser Val Val Thr Val Pro Ser Ser Ser Leu Gly
        180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser Gln Glu Asp Pro Glu Val Gln Phe Asn Trp
        260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
        420                 425                 430

Gln Lys Ser Leu Ser Leu Ser Leu Gly Lys
            435                 440

<210> SEQ ID NO 14
<211> LENGTH: 442
<212> TYPE: PRT
<213> ORGANISM: Homo sapiens

<400> SEQUENCE: 14

Glu Val Lys Val Val Glu Ser Gly Gly Gly Leu Val Gln Pro Gly Gly
1               5                   10                  15

Ser Leu Lys Leu Ser Cys Val Val Ser Gly Phe Thr Phe Ser Asn Tyr
            20                  25                  30

Trp Val Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Glu Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 15
<211> LENGTH: 442
<212> TYPE: PRT
<213> ORGANISM: Homo sapiens

<400> SEQUENCE: 15

Glu Val Gln Val Val Glu Ser Gly Gly Gly Leu Val Gln Pro Gly Gly
1               5                   10                  15

Ser Leu Lys Leu Ser Cys Val Val Ser Gly Phe Thr Phe Ser Asn Tyr

```
                  20                  25                  30
Trp Val Asn Trp Val Arg Gln Ala Pro Gly Lys Gly Leu Glu Trp Val
             35                  40                  45
Ala Gln Ile Arg Leu Lys Ser Asp Asn Tyr Ala Thr His Tyr Glu Glu
 50                  55                  60
Ser Val Lys Gly Arg Phe Thr Ile Ser Arg Asp Asp Ser Lys Asn Ser
 65                  70                  75                  80
Val Tyr Leu Gln Met Asn Ser Leu Arg Ala Glu Asp Thr Ala Ile Tyr
                 85                  90                  95
Tyr Cys Thr Asn Trp Glu Asp Tyr Trp Gly Gln Gly Thr Thr Val Thr
                100                 105                 110
Val Ser Ser Ala Ser Thr Lys Gly Pro Ser Val Phe Pro Leu Ala Pro
                115                 120                 125
Cys Ser Arg Ser Thr Ser Glu Ser Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                    165                 170                 175
Leu Tyr Ser Leu Ser Ser Val Val Thr Val Pro Ser Ser Ser Leu Gly
                180                 185                 190
Thr Lys Thr Tyr Thr Cys Asn Val Asp His Lys Pro Ser Asn Thr Lys
                195                 200                 205
Val Asp Lys Arg Val Glu Ser Lys Tyr Gly Pro Pro Cys Pro Pro Cys
                210                 215                 220
Pro Ala Pro Glu Phe Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                    245                 250                 255
Val Val Val Asp Val Ser Gln Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Tyr Arg Val Val Ser Val Leu Thr Val Leu
                290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                    325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
                370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                    405                 410                 415
Val Phe Ser Cys Ser Val Met His Glu Ala Leu His Asn His Tyr Thr
                420                 425                 430
Gln Lys Ser Leu Ser Leu Ser Leu Gly Lys
                435                 440
```

<210> SEQ ID NO 16
<211> LENGTH: 442
<212> TYPE: PRT
<213> ORGANISM: Homo sapiens

<400> SEQUENCE: 16

```
Glu Val Gln Leu Val Glu Ser Gly Gly Gly Leu Val Gln Pro Gly Gly
1               5                   10                  15

Ser Leu Lys Leu Ser Cys Val Val Gly Phe Thr Phe Ser Asn Tyr
                20                  25                  30

Trp Val Asn Trp Val Arg Gln Ala Pro Gly Lys Gly Leu Glu Trp Val
            35                  40                  45

Ala Gln Ile Arg Leu Lys Ser Asp Asn Tyr Ala Thr His Tyr Glu Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Ile Tyr
                85                  90                  95

Tyr Cys Thr Asn Trp Glu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
```

```
                370              375              380
Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

<210> SEQ ID NO 17
<211> LENGTH: 218
<212> TYPE: PRT
<213> ORGANISM: Homo sapiens

<400> SEQUENCE: 17

```
Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Asn Ile His
65                  70                  75                  80

Pro Leu Glu Glu Glu Asp Phe Ala Thr Tyr Tyr Cys His His Ser Trp
                85                  90                  95

Glu Ile Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 18
<211> LENGTH: 218
<212> TYPE: PRT
<213> ORGANISM: Homo sapiens

<400> SEQUENCE: 18

```
Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
```

```
            35                  40                  45
Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Asn Ile His
 65                  70                  75                  80

Pro Leu Glu Pro Glu Asp Phe Ala Thr Tyr Tyr Cys His His Ser Trp
                 85                  90                  95

Glu Ile Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 19
<211> LENGTH: 218
<212> TYPE: PRT
<213> ORGANISM: Homo sapiens

<400> SEQUENCE: 19

Asp Ile Val Leu Thr Gln Ser Pro Asp Ser Leu Ala Val Ser Leu Gly
 1               5                  10                  15

Glu Arg Ala Thr Ile Ser Cys Arg Ala Ser Gln Ser Val Ser Thr Ser
                 20                  25                  30

Arg Tyr Ser Tyr Ile His Trp Tyr Gln Gln Lys Pro Gly Gln Pro Pro
            35                  40                  45

Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys His His Ser Trp
                 85                  90                  95

Glu Ile Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 20
<211> LENGTH: 218
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Arg Tyr Ser Tyr Ile His Trp Tyr Gln Gln Lys Pro Gly Gln Pro Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys His His Ser Trp
                85                  90                  95

Glu Ile Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 60
<212> TYPE: PRT
<213> ORGANISM: Homo sapiens

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly
    50                  55                  60

<210> SEQ ID NO 22
<211> LENGTH: 60

```
<212> TYPE: PRT
<213> ORGANISM: Homo sapiens

<400> SEQUENCE: 22

Met Ala Glu Pro Arg Gln Glu Phe Asp Val Met Glu Asp His Ala Gly
1               5                   10                  15

Thr Tyr Gly Leu Gly Asp Arg Lys Asp Gln Gly Gly Tyr Thr Met Leu
            20                  25                  30

Gln Asp Gln Glu Gly Asp Thr Asp Ala Gly Leu Lys Glu Ser Pro Leu
        35                  40                  45

Gln Thr Pro Ala Glu Asp Gly Ser Glu Glu Leu Gly
    50                  55                  60

<210> SEQ ID NO 23
<211> LENGTH: 60
<212> TYPE: PRT
<213> ORGANISM: Mus musculus

<400> SEQUENCE: 23

Met Ala Asp Pro Arg Gln Glu Phe Asp Thr Met Glu Asp His Ala Gly
1               5                   10                  15

Thr Tyr Gly Leu Gly Asp Arg Lys Asp Gln Gly Asp Tyr Thr Leu Leu
            20                  25                  30

Gln Asp Gln Glu Gly Asp Met Asp His Gly Leu Lys Glu Ser Pro Pro
        35                  40                  45

Gln Pro Pro Ala Asp Asp Gly Ala Glu Glu Pro Gly
    50                  55                  60

<210> SEQ ID NO 24
<211> LENGTH: 15
<212> TYPE: PRT
<213> ORGANISM: Homo sapiens

<400> SEQUENCE: 24

Asp His Ala Gly Thr Tyr Gly Leu Gly Asp Arg Lys Asp Gln Gly
1               5                   10                  15

<210> SEQ ID NO 25
<211> LENGTH: 15
<212> TYPE: PRT
<213> ORGANISM: Homo sapiens

<400> SEQUENCE: 25

Asp His Ala Gly Thr Tyr Gly Leu Gly Ala Ala Lys Asp Gln Gly
1               5                   10                  15

<210> SEQ ID NO 26
<211> LENGTH: 15
<212> TYPE: PRT
<213> ORGANISM: Homo sapiens

<400> SEQUENCE: 26

His Ala Gly Thr Tyr Gly Leu Gly Asp Arg Lys Asp Gln Gly Gly
1               5                   10                  15

<210> SEQ ID NO 27
<211> LENGTH: 15
<212> TYPE: PRT
<213> ORGANISM: Homo sapiens

<400> SEQUENCE: 27

His Ala Gly Thr Tyr Gly Leu Gly Asp Ala Ala Asp Gln Gly Gly
```

```
                1               5                  10                 15
```

<210> SEQ ID NO 28
<211> LENGTH: 15
<212> TYPE: PRT
<213> ORGANISM: Homo sapiens

<400> SEQUENCE: 28

```
Ala Gly Thr Tyr Gly Leu Gly Asp Arg Lys Asp Gln Gly Gly Tyr
1               5                   10                  15
```

<210> SEQ ID NO 29
<211> LENGTH: 15
<212> TYPE: PRT
<213> ORGANISM: Homo sapiens

<400> SEQUENCE: 29

```
Ala Gly Thr Tyr Gly Leu Gly Asp Arg Ala Ala Gln Gly Gly Tyr
1               5                   10                  15
```

<210> SEQ ID NO 30
<211> LENGTH: 15
<212> TYPE: PRT
<213> ORGANISM: Homo sapiens

<400> SEQUENCE: 30

```
Gly Thr Tyr Gly Leu Gly Asp Arg Lys Asp Gln Gly Gly Tyr Thr
1               5                   10                  15
```

<210> SEQ ID NO 31
<211> LENGTH: 15
<212> TYPE: PRT
<213> ORGANISM: Homo sapiens

<400> SEQUENCE: 31

```
Gly Thr Tyr Gly Leu Gly Asp Arg Lys Ala Ala Gly Gly Tyr Thr
1               5                   10                  15
```

<210> SEQ ID NO 32
<211> LENGTH: 15
<212> TYPE: PRT
<213> ORGANISM: Homo sapiens

<400> SEQUENCE: 32

```
Thr Tyr Gly Leu Gly Asp Arg Lys Asp Gln Gly Gly Tyr Thr Met
1               5                   10                  15
```

<210> SEQ ID NO 33
<211> LENGTH: 15
<212> TYPE: PRT
<213> ORGANISM: Homo sapiens

<400> SEQUENCE: 33

```
Thr Tyr Gly Leu Gly Asp Arg Lys Asp Ala Ala Gly Tyr Thr Met
1               5                   10                  15
```

<210> SEQ ID NO 34
<211> LENGTH: 15
<212> TYPE: PRT
<213> ORGANISM: Homo sapiens

<400> SEQUENCE: 34

```
Tyr Gly Leu Gly Asp Arg Lys Asp Gln Gly Gly Tyr Thr Met His
1               5                   10                  15
```

```
<210> SEQ ID NO 35
<211> LENGTH: 15
<212> TYPE: PRT
<213> ORGANISM: Homo sapiens

<400> SEQUENCE: 35

Tyr Gly Leu Gly Asp Arg Lys Asp Gln Ala Ala Tyr Thr Met His
1               5                   10                  15

<210> SEQ ID NO 36
<211> LENGTH: 15
<212> TYPE: PRT
<213> ORGANISM: Homo sapiens

<400> SEQUENCE: 36

Gly Leu Gly Asp Arg Lys Asp Gln Gly Gly Tyr Thr Met His Gln
1               5                   10                  15

<210> SEQ ID NO 37
<211> LENGTH: 15
<212> TYPE: PRT
<213> ORGANISM: Homo sapiens

<400> SEQUENCE: 37

Gly Leu Gly Asp Arg Lys Asp Gln Gly Ala Ala Thr Met His Gln
1               5                   10                  15

<210> SEQ ID NO 38
<211> LENGTH: 15
<212> TYPE: PRT
<213> ORGANISM: Homo sapiens

<400> SEQUENCE: 38

Leu Gly Asp Arg Lys Asp Gln Gly Gly Tyr Thr Met His Gln Asp
1               5                   10                  15

<210> SEQ ID NO 39
<211> LENGTH: 15
<212> TYPE: PRT
<213> ORGANISM: Homo sapiens

<400> SEQUENCE: 39

Leu Gly Asp Arg Lys Asp Gln Gly Gly Ala Ala Met His Gln Asp
1               5                   10                  15

<210> SEQ ID NO 40
<211> LENGTH: 15
<212> TYPE: PRT
<213> ORGANISM: Homo sapiens

<400> SEQUENCE: 40

Gly Asp Arg Lys Asp Gln Gly Gly Tyr Thr Met His Gln Asp Gln
1               5                   10                  15

<210> SEQ ID NO 41
<211> LENGTH: 15
<212> TYPE: PRT
<213> ORGANISM: Homo sapiens

<400> SEQUENCE: 41

Gly Asp Arg Lys Asp Gln Gly Gly Tyr Ala Ala His Gln Asp Gln
1               5                   10                  15

<210> SEQ ID NO 42
```

```
<211> LENGTH: 15
<212> TYPE: PRT
<213> ORGANISM: Homo sapiens

<400> SEQUENCE: 42

Asp Arg Lys Asp Gln Gly Gly Tyr Thr Met His Gln Asp Gln Glu
1               5                   10                  15

<210> SEQ ID NO 43
<211> LENGTH: 15
<212> TYPE: PRT
<213> ORGANISM: Homo sapiens

<400> SEQUENCE: 43

Asp Arg Lys Asp Gln Gly Gly Tyr Thr Ala Ala Gln Asp Gln Glu
1               5                   10                  15

<210> SEQ ID NO 44
<211> LENGTH: 15
<212> TYPE: PRT
<213> ORGANISM: Homo sapiens

<400> SEQUENCE: 44

Arg Lys Asp Gln Gly Gly Tyr Thr Met His Gln Asp Gln Glu Gly
1               5                   10                  15

<210> SEQ ID NO 45
<211> LENGTH: 15
<212> TYPE: PRT
<213> ORGANISM: Homo sapiens

<400> SEQUENCE: 45

Arg Lys Asp Gln Gly Gly Tyr Thr Met Ala Ala Asp Gln Glu Gly
1               5                   10                  15

<210> SEQ ID NO 46
<211> LENGTH: 15
<212> TYPE: PRT
<213> ORGANISM: Homo sapiens

<400> SEQUENCE: 46

Lys Asp Gln Gly Gly Tyr Thr Met His Gln Asp Gln Glu Gly Asp
1               5                   10                  15

<210> SEQ ID NO 47
<211> LENGTH: 15
<212> TYPE: PRT
<213> ORGANISM: Homo sapiens

<400> SEQUENCE: 47

Lys Asp Gln Gly Gly Tyr Thr Met His Ala Ala Gln Glu Gly Asp
1               5                   10                  15

<210> SEQ ID NO 48
<211> LENGTH: 15
<212> TYPE: PRT
<213> ORGANISM: Homo sapiens

<400> SEQUENCE: 48

Asp Gln Gly Gly Tyr Thr Met His Gln Asp Gln Glu Gly Asp Thr
1               5                   10                  15

<210> SEQ ID NO 49
<211> LENGTH: 15
<212> TYPE: PRT
```

```
<213> ORGANISM: Homo sapiens

<400> SEQUENCE: 49

Asp Gln Gly Gly Tyr Thr Met His Gln Ala Ala Glu Gly Asp Thr
1               5                   10                  15

<210> SEQ ID NO 50
<211> LENGTH: 15
<212> TYPE: PRT
<213> ORGANISM: Homo sapiens

<400> SEQUENCE: 50

Gln Gly Gly Tyr Thr Met His Gln Asp Gln Glu Gly Asp Thr Asp
1               5                   10                  15

<210> SEQ ID NO 51
<211> LENGTH: 15
<212> TYPE: PRT
<213> ORGANISM: Homo sapiens

<400> SEQUENCE: 51

Gln Gly Gly Tyr Thr Met His Gln Asp Ala Ala Gly Asp Thr Asp
1               5                   10                  15

<210> SEQ ID NO 52
<211> LENGTH: 15
<212> TYPE: PRT
<213> ORGANISM: Homo sapiens

<400> SEQUENCE: 52

Gly Gly Tyr Thr Met His Gln Asp Gln Glu Gly Asp Thr Asp Ala
1               5                   10                  15

<210> SEQ ID NO 53
<211> LENGTH: 15
<212> TYPE: PRT
<213> ORGANISM: Homo sapiens

<400> SEQUENCE: 53

Gly Gly Tyr Thr Met His Gln Asp Gln Ala Ala Asp Thr Asp Ala
1               5                   10                  15

<210> SEQ ID NO 54
<211> LENGTH: 15
<212> TYPE: PRT
<213> ORGANISM: Homo sapiens

<400> SEQUENCE: 54

Gly Tyr Thr Met His Gln Asp Gln Glu Gly Asp Thr Asp Ala Gly
1               5                   10                  15

<210> SEQ ID NO 55
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 55

Gly Gly Gly Gly Ser
1               5
```

HUMANIZED ANTI-TAU ANTIBODIES

CROSS-REFERENCE TO RELATED APPLICATIONS

This application is a continuation of International Application No. PCT/US2015/038002, filed on Jun. 26, 2015, which claims benefit of priority under 35 U.S.C. § 119(e) of U.S. Ser. No. 62/170,036, filed Jun. 27, 2014, U.S. Ser. No. 62/080,903, filed Nov. 17, 2014, and U.S. Ser. No. 62/018,436, filed Jun. 2, 2015, the entire contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 12, 2017, is named 397835-215C1 (156248)_SL.txt and is 43,034 bytes in size.

FIELD OF THE INVENTION

The present invention relates to the field of humanized antibodies and antigen-binding fragments thereof that bind to tau and methods of using such antibodies to treat tauopathies. In particular, the present invention relates to a humanized antibody and antigen-binding fragments that bind to specific epitopes of tau and prevent tau seeding.

BACKGROUND OF THE INVENTION

Tauopathies have in common the accumulation of insoluble, hyperphosphorylated tau protein in the brain. More than 20 different neurodegenerative disorders are characterized by some degree of neurofibrillary degeneration and can be classified as tauopathies (Williams 2006). Prototypical tauopathies, such as progressive supranuclear palsy (PSP) and corticobasal degeneration (CBD) are characterized by tau inclusions being the sole or predominant central nervous system lesions. Prototypical tauopathies differ from other tauopathies where tau aggregates are found in the presence of other neuropathological features, like the amyloid beta (Aβ) plaques found in Alzheimer's disease (AD) or the Lewy bodies found in Parkinson's disease (PD). In these non-prototypical tauopathies, it is more uncertain if the tau pathology represents the primary disease driver or if it is secondary to other protein misfolding and neurodegeneration.

Progressive supranuclear palsy (PSP, also known as Steele-Richardson-Olszewski syndrome) is a progressive neurodegenerative disorder, with an estimated annual incidence of 5-7 per 100,000 (Golbe 2014). Within the US, the disease affects approximately 20,000 individuals. There is no apparent geographical, ethnic, gender, or racial disparity in PSP frequency. PSP can initially present with clinical symptoms similar to other brain disorders, including idiopathic Parkinson's disease. For this reason, correct diagnosis of PSP is sometimes delayed, usually taking place 1 to 3 years after the initial onset of clinical symptoms. Symptom onset is most often between the ages of 50 to 70 years and although the clinical course is variable, the typical survival from time of symptom onset is 5 to 9 years (Houghton, 2007). Though heterogeneity in clinical presentation exists, the most common and initially described PSP syndrome, now referred to as Richardson's Syndrome, are the presence of prominent postural instability and axial rigidity leading to falls, supranuclear gaze palsy causing range of vision impairment, frontal-subcortical dementia, and dysphagia leading to aspiration. The course of disease is progressive and uniformly fatal (Williams and Lees 2009).

Pathologically, PSP is characterized by the abnormal accumulation of hyper phosphorylated, insoluble aggregates of tau protein in neurons and glia in the brainstem, cerebellum, basal ganglia, and cerebral cortex (Williams and Lees 2009). The degree and distribution of tau aggregation in PSP is strongly correlated with PSP symptomatology during life (Schofield et al. 2012). The National Institute of Neurological Disorders and the Society for Progressive Supranuclear Palsy (NINDS-SPSP) research criteria which describe Richardson's Syndrome are highly predictive of underlying PSP pathology (Litvan et al. 1996). Neuronal loss in various regions of the brain accompanies neurofibrillary tangles (NFTs) that are composed of tau aggregates. Multiple neurotransmitter abnormalities arise as well, including those affecting specific dopaminergic, cholinergic, GABAergic, and noradrenergic systems.

There are no currently approved treatments for PSP (Stamelou et al. 2010). The negative outcomes of therapeutic efficacy studies in PSP preclude recommending an evidence-based standard therapy (Boxer et al. 2014). In the absence of any effective disease modifying or neuroprotective therapies, PSP represents an urgent unmet medical need.

Alzheimer's disease (AD) is a common chronic progressive neurodegenerative disease in which there is an irreversible loss of cognitive and behavioral functions. The disease can persevere for over 10 years, advancing from mild symptoms to extremely severe manifestations. AD is said to afflict approximately 10% of the population over the age of 65 and more than 30% of the population over the age of 80. Alzheimer's disease presents itself pathologically as extracellular amyloid plaques and intracellular neurofibrillary tangles. The neurofibrillary tangles are composed, e.g., of the microtubule-binding protein tau, which is assembled into paired helical and straight filaments. It has been suggested that these entities may be functionally linked, although the mechanisms by which amyloid deposition promotes pathological tau filament assembly, or vice versa, is not clear.

The intracellular neurofibrillary structures of tauopathies (neurofibrillary tangles, dystrophic neurites, and neurophil threads) have paired helical filaments (PHFs). The major protein subunit of the PHFs is microtubule associated protein tau in abnormally hyperphosphorylated form. Neurons with neurofibrillary changes degenerate, and the degree of this degeneration directly correlates with the degree of dementia in the affected individuals.

Other tauopathies known to have filamentous cellular inclusions containing microtubule associated protein tau include Pick's disease (PiD), a group of related disorders collectively termed frontotemporal dementia with Parkinsonism linked to chromosome 17 (FTDP-17), amyotropic lateral sclerosis (ALS), Creutzfeldt-Jakob disease (CJD), dementia pugilistica (DP), Gerstmann-Straussler-Scheinker disease (GSSD), Lewy body disease, chronic traumatic encephalopathy (CTE), and Huntington disease. Although the etiology, clinical symptoms, pathologic findings and the biochemical composition of filamentous cellular inclusions in these diseases are different, there is emerging evidence suggesting that the mechanisms involved in aggregation of normal cellular proteins to form various filamentous inclusions being comparable. It is believed, that an initial alteration in conformation of microtubule associated protein tau, acts to initiate the generation of nuclei or seeds for filament assembly, is one of the key features. This process can be

SUMMARY OF THE INVENTION

As one aspect of the present invention, an isolated antibody or antigen-binding fragment that specifically binds tau is provided. The antibody or fragment comprises a heavy chain variable (VH) region and a light chain variable (VL) region, and each of the VH and VL regions have a sequence selected from amino acid sequences set forth in FIGS. 1 and 2. More particularly, the VL region can have an amino acid sequence selected from the group consisting of SEQ ID NOs: 1, 2, 3 and 4 [VK1, VK2, VK3, and VK4], and the VH region can have an amino acid sequence selected from the group consisting of SEQ ID NOs: 5, 6, 7 and 8 [VH1, VH2, VH3, and VH4]. In some embodiments, the VL region has an amino acid sequence of SEQ ID NO: 2 [VK2] and the VH region has an amino acid sequence of SEQ ID NO: 5 [VH1]. In some embodiments, the antibody comprises an Fc region, which may be of human IgG1, IgG2, IgG3, IgG4 or variants thereof, such as a human IgG4 containing a S241P hinge stabilizing mutation. The antibody can comprise a light chain constant region of human isotype kappa or variants thereof. In some embodiments, the antibody or fragment is scFv or Fab. In some embodiments, the antibody or fragment is a humanized antibody or fragment or a chimeric antibody or fragment. The antibody or fragment may be a monoclonal antibody. In some embodiments, the antibody or fragment competes with HJ8.5 for specific binding to human tau protein. In some embodiments, the antibody or fragment binds human tau protein with an equilibrium dissociation constant (Kd) of at least $10^{-4}$M.

As another aspect of the present invention, a multi-specific antibody or antigen-binding fragment having a plurality of antigen-binding regions is provided. At least one antigen-binding region of the multi-specific antibody or fragment binds to human tau protein. Alternatively, a bispecific antibody or antigen-binding fragment having two antigen-binding regions is provided. One of the antigen-binding regions of the bispecific antibody or fragment binds to human tau protein. Alternatively, a bispecific antibody or antigen-binding fragment is provided where one arm of the antibody or antigen-binding fragment competes with HJ8.5 for specific binding to human tau protein. Alternatively, a bispecific antibody or antigen-binding fragment is provided where one arm of the antibody or antigen-binding fragment is comprised of a heavy chain variable (VH) region and a light chain variable (VL) region, wherein each of the VH and VL regions have a sequence selected from amino acid sequences set forth in FIGS. 1 and 2.

Any of the foregoing antibodies or antigen-binding fragments may further comprise a toxic payload, optionally a drug conjugate, or a radionuclide.

As yet another aspect of the present invention, an isolated nucleic acid molecule is provided which encodes any of the foregoing antibodies or antigen-binding fragment, or a VH region or VL region set forth in FIG. 1 or 2. A vector (such as an expression vector) comprising such a nucleic acid molecule may be provided. An isolated host cell comprising such a vector may be provided. The host cell may be a prokaryotic or eukaryotic cell, such as a mammalian cell.

As another aspect of the present invention, a pharmaceutical composition is provided. The pharmaceutical composition comprises any of the foregoing antibodies or antigen-binding fragments, or a nucleic acid molecule as described herein, and a pharmaceutically acceptable carrier.

As yet another aspect of the present invention, an isolated amino acid sequence is provided containing the sequence of one of the light chains as set forth in FIGS. 1 and 2. Alternatively or additionally, an isolated amino acid sequence is provided containing the sequence of one of heavy chains as set forth in FIGS. 1 and 2.

As a further aspect of the present invention, an isolated humanized antibody or antigen-binding fragment is provided that specifically binds an epitope comprising the amino acid sequence DQGGYT (SEQ ID NO: 9). The antibody or antigen-binding fragment may contain CDRs of the VH and VL regions are from a donor antibody. In some embodiments, the antibody comprises an Fc region, such as the Fe region is of IgG1, IgG2, IgG3, IgG4 or variant thereof. The Fc region may be a human IgG4 or variant thereof, such a human IgG4 containing the S241P hinge stabilizing mutation. The antibody can comprise a light chain constant region of human isotype kappa or variants thereof. In some embodiments, the antibody or fragment is scFv or Fab. In some embodiments, the antibody or fragment is a humanized antibody or fragment or a chimeric antibody or fragment. The antibody or fragment may be a monoclonal antibody. The antibody or fragment may be a bispecific antibody or antigen-binding fragment where one arm of the antibody or fragment specifically binds an epitope comprising the amino acid sequence DQGGYT (SEQ ID NO: 9). In some embodiments, an immunoconjugate is provided comprising one of the foregoing antibodies or fragments linked to a detectable or therapeutic moiety.

As another aspect, an isolated humanized antibody or antigen-binding fragment is provided that specifically binds an epitope comprising the amino acid sequence GYTMHQDQ (SEQ ID NO: 10). The antibody or fragment can have CDRs of the VH and VL regions from a donor antibody. In some embodiments, the antibody or fragment comprises an Fc region, such as an Fc region of IgG1, IgG2, IgG3, IgG4 or a variant thereof. The Fc region may be a human IgG4 and variants thereof containing the S241P hinge stabilizing mutation. The antibody may comprise a light chain constant region. In some embodiments, the antibody or fragment is an scFv or Fab. A bispecific antibody or antigen-binding fragment is also provided where one arm of the antibody specifically binds an epitope comprising the amino acid sequence GYTMHQDQ (SEQ ID NO: 10). In some embodiments, an immunoconjugate comprising any of the foregoing antibodies or fragments is linked to a detectable or therapeutic moiety.

As a further aspect of the present invention, a method of preventing or treating a tauopathy in a subject, comprising administering to a human in need of therapy for a tauopathy with one or more of the antibodies or fragments described herein. The antibodies or antigen-binding fragment are administered under conditions and in an amount effective to prevent or treat the tauopathy. The tauopathy may be one or more of Alzheimer's disease (AD), progressive supranuclear palsy (PSP), corticobasal degeneration (CBD), Pick's disease (PiD), a group of related disorders collectively termed frontotemporal dementia with Parkinsonism linked to chromosome 17 (FTDP-17), amyotropic lateral sclerosis (ALS), Creutzfeldt-Jakob disease (CJD), dementia pugilistica (DP), Gerstmann-Straussler-Scheinker disease (GSSD), Lewy body disease, chronic traumatic encephalopathy (CTE), or Huntington disease.

A method is provided for treating a tauopathy comprising administering an anti-tau antibody or fragment to a subject in need of treatment, wherein the antibody or antigen-binding fragment specifically binds tau and comprises a heavy chain variable (VH) region and a light chain variable (VL) region, wherein each of the VH and VL regions have a sequence selected from amino acid sequences set forth in FIGS. 1 and 2, and the antibody or fragment is administered in a dose of from about 0.1 mg/kg to about 250 mg/kg to the subject, alternatively from about 1 mg/kg to about 25 mg/kg. In some embodiments, the antibody or fragment has a VL region comprising an amino acid sequence selected from the group consisting of SEQ ID NOs: 1, 2, 3 and 4 [VK1, VK2, VK3, and VK4]; alternatively or additionally, the antibody or fragment has a VH region comprising an amino acid sequence selected from the group consisting of SEQ ID NOs: 5, 6, 7 and 8 [VH1, VH2, VH3, and VH4].

BRIEF DESCRIPTION OF THE DRAWINGS

FIG. 1 shows the variable region sequences of the murine HJ8.5 antibody as well as 4 humanized variant sequences for each of the heavy and light chains (4 VH and 4 VL/VK sequences). FIG. 1 shows sequences for MuVL (SEQ ID NO:11); VK1 (SEQ ID NO:1); VK2 (SEQ ID NO:2); VK3 (SEQ ID NO:3); VK4 (SEQ ID NO:4); MuVH (SEQ ID NO:12); VH1 (SEQ ID NO:5); VH2 (SEQ ID NO:6); VH3 (SEQ ID NO:7); VH4 (SEQ ID NO:8).

FIG. 2A shows the sequence of the humanized variable and constant region sequences for the heavy chains VH1 (SEQ ID NO:13). FIG. 2B shows the sequence of the humanized variable and constant region sequences for the heavy chain VH2 (SEQ ID NO:14). FIG. 2C shows the sequence of the humanized variable and constant region sequences for the heavy chain VH3 (SEQ ID NO:15). FIG. 2D shows the sequence of the humanized variable and constant region sequences for the heavy chain VH4 (SEQ ID NO:16). The variable heavy chain is grafted to the constant heavy chain of human IgG4 containing a S241P hinge stabilizing mutation. FIG. 2E shows the sequence of the humanized variable and constant region sequences for the heavy chain VL1 (SEQ ID NO: 17). FIG. 2F shows the sequence of the humanized variable and constant region sequences for the heavy chain VL2 (SEQ ID NO:18). FIG. 2G shows the sequence of the humanized variable and constant region sequences for the heavy chain VL3 (SEQ ID NO:19). FIG. 2H shows the sequence of the humanized variable and constant region sequences for the heavy chain VL4 (SEQ ID NO:20).

FIG. 3 shows expression data from two rounds of transient expression of cells transfected with polynucleotides encoding VH and VK regions. Results are summarized for 13 humanized anti tau antibodies based on different combinations of humanized heavy and light variable regions, with different levels of expression being observed.

FIG. 4 shows data from a potency assay that evaluates the ability of the present anti-tau antibodies to compete with the original murine HJ8.5 (parent antibody) for binding to human tau in an ELISA type format.

FIG. 5 summarizes the results from surface plasmon resonance (SPR) analysis, determining the binding kinetics of the six best expressing humanized constructs against human tau.

FIGS. 7A to 7MM show binding of humanized and control antibodies to tissue from wild type mice (negative control tissue), P301S mice (which express human tau having a P301S mutation and develop age associated tau pathology), and humans with either Alzheimer's disease or Progressive Supranuclear Palsy (PSP). FIGS. 7A, 7B, 7C, 7D and 7E show binding of chimera (positive control) to mouse and human tissue; FIGS. 7F, 7G, 7H and 7I show binding of non-specific human IgG4 (negative control) to mouse and human tissue. FIGS. 7J, 7K, 7L, 7M, and 7N show binding of VH1/VK2 to mouse and human tissue. FIGS. 7O, 7P, 7Q, 7R and 7S show binding of VH1/VK3 to mouse and human tissue. FIGS. 7T, 7U, 7V, 7W and 7X show binding of VH2/VK2 to mouse and human tissue. FIGS. 7Y, 7Z, 7AA, 7BB and 7CC show binding of VH2/VK3 to mouse and human tissue. FIGS. 7DD, 7EE, 7FF, 7GG and 7HH show binding of VH3/VK2 to mouse and human tissue. FIGS. 7II, 7JJ, 7KK, 7LL and 7MM show binding of VH3/VK3 to mouse and human tissue.

FIG. 8 shows human, rhesus monkey and mouse tau sequences (SEQ ID NOs:21, 22, 23, respectively).

FIG. 9 shows the detailed peptide based epitope mapping of HJ8.5 and $C_2$N-8E12. The mapping indicates that the binding epitope of $C_2$N-8E12 is $_{25}$DQGGYT$_{30}$ (SEQ ID NO: 9) and matches the epitope of the murine parent, HJ8.5. FIG. 9 shows sequences of peptides PEP_2875800 to PEP_2875830 (SEQ ID NOs:24 to 54, respectively).

DESCRIPTION OF THE INVENTION

Figure 6:
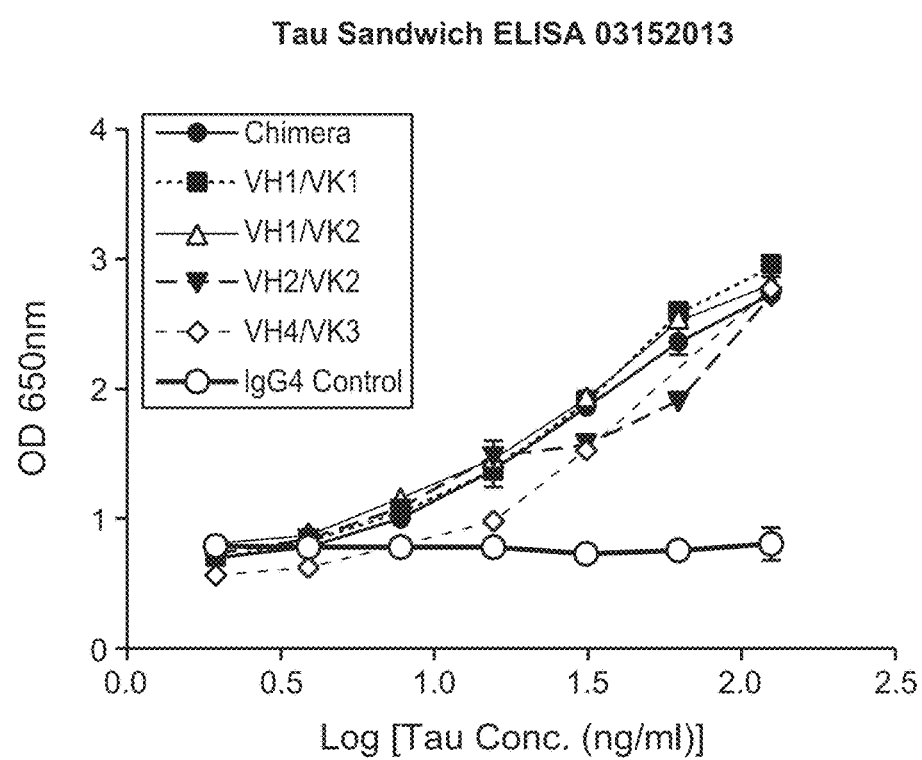
FIG. 6 shows the binding of four humanized antibody variants to soluble human tau in a sandwich style ELISA.
Figure 7D:
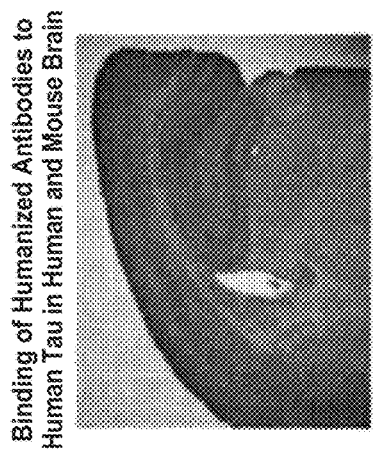
Figure 7E:
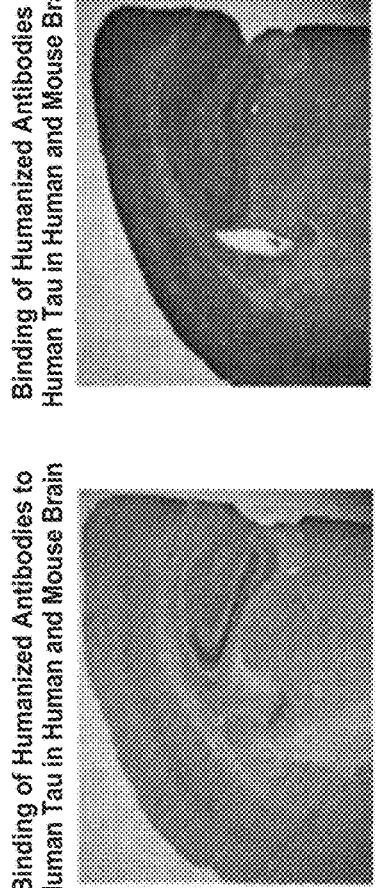
Figure 7F:
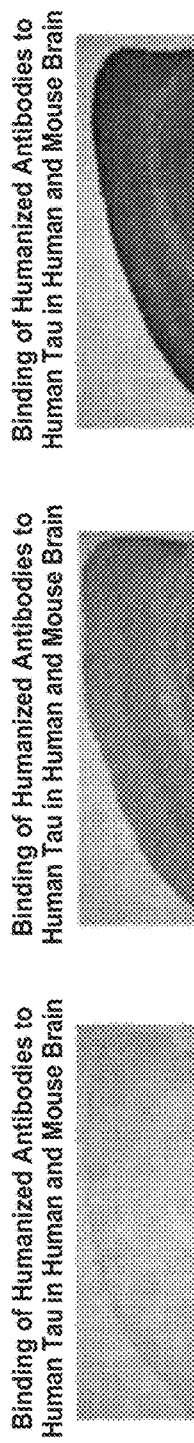
Figure 7G:
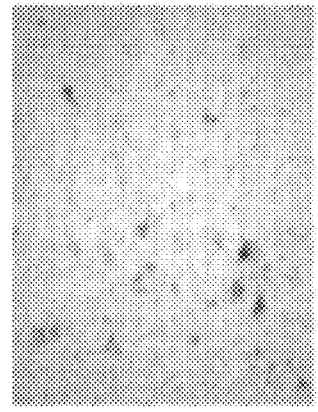
Figure 7H:
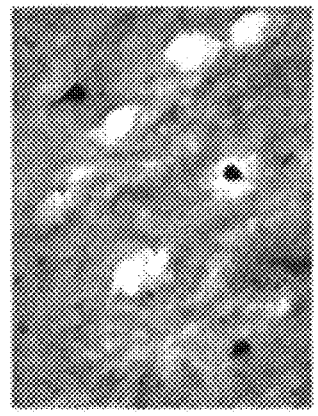

Strong experimental evidence and biological rationale exists to support the tau immunotherapy strategy as a way to counter tau pathology in neurodegeneration. First, tau is normally a highly soluble, natively unfolded, and intracellular protein, so an extracellular antibody is unlikely to affect the normal functions of tau. Second, the burden of tau pathology correlates with progressive neuronal dysfunction, synaptic loss, and functional decline in humans and transgenic mouse models of tauopathy. Third, under pathological conditions, tau becomes misfolded and aggregates into intraneuronal neurofibrillary tangles (NFTs) composed of pathological tau fibrils. In human tauopathies, this pathology progresses from one brain region to another in disease-specific patterns. Experimental data suggests that tau aggregates can spread from cell to cell to induce further tau aggregation and spreading of tau pathology in brain. This data suggests that aggregates produced in one cell are released into the extracellular space and can promote aggregation in neighboring or connected cells. Finally, prior art exists demonstrating that anti-tau antibodies can prevent or slow the progression of tau pathology in the brain of mice that carry a mutated human form of tau.

A "humanized antibody" is an antibody or a variant, derivative, analog or fragment thereof which has been modified to reduce the risk of the non-human antibody eliciting an immune response in humans following administration. A humanized antibody, as used herein, immunospecifically binds to the same or similar epitope as a non-human antibody (donor antibody). In some embodiments a humanized antibody comprises a framework (FR) region having substantially the amino acid sequence of a human antibody and a complementary determining region (CDR) having substantially the amino acid sequence of a non-human antibody. The term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. A humanized antibody that comprises a novel framework region is provided in the invention.

In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The antibody or antigen-binding fragment thereof is selected from the group consisting of: a disulfide linked Fv, a monoclonal antibody, a single-chain variable fragment (scFv), a chimeric antibody, a CDR-grafted antibody, a diabody, a humanized antibody, a multispecific antibody, a Fab (fragment antigen-binding), a bispecific antibody, a F(ab')2 (a dual arm, antigen-binding fragment typically prepared by cleavage of an antibody with pepsin), a Fab'(the result of splitting a F(ab')2 into two antigen-binding fragments, typically by mild reduction), or a Fv (an antigen-binding variable fragment).

The term "chimeric antibody" refers to antibodies which comprise heavy and light chain variable region sequences from one species and constant region sequences from another species, such as antibodies having murine heavy and light chain variable regions linked to human constant regions.

A "VH region", "VL region" or "VK region" refers to the variable region of the heavy chain (VH), the variable region of the light lambda chain (VL) or the variable region of the light kappa chain (VK), respectively. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. A FR represents one of the four sub-regions, and FRs represents two or more of the four sub-regions constituting a framework region.

Many humanized immunoglobulins that have been previously described (Jones et al., Verhoeyen et al., Riechmann et al.) have comprised a framework that is identical to the framework of a particular human immunoglobulin chain, the acceptor, and three CDR's from a non-human donor immunoglobulin chain. A "humanized anti-tau" antibody refers to an antibody that has been generated from a non-human (donor) antibody capable of binding tau and said binding is transferred to a human antibody (acceptor).

The term "CDR" refers to the complementarity determining region within antibody variable sequences. There are three CDRs in each of the variable regions of the heavy chain and the light chain, which are designated CDR1, CDR2 and CDR3, for each of the variable regions. The amino acid sequences of the CDRs of the VH and VL/K regions of the claimed invention are set forth in FIG. 1.

As used herein, the term single-chain Fv, also termed single-chain antibody, refers to engineered antibody constructs prepared by isolating the binding domains (both heavy and light chain) of a binding antibody, and supplying a linking moiety which permits preservation of the binding function. A linker peptide inserted between the two chains allows for the stabilization of the variable domains without interfering with the proper folding and creation of an active binding site. This linker can be between 5 and 30 amino acids long and typically consist of repeats of "GGGGS" ((Gly)4Ser) amino acid sequence (SEQ ID NO: 55). This forms, in essence, a radically abbreviated antibody, having only the variable domain necessary for binding the antigen.

Diabodies, triabodies, and tetrabodies and higher order variants are typically created by varying the length of the linker peptide referred to above, from zero to several amino acids. The variants are multivalent, multispecific antibodies in which VH and VL domains are expressed on a polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2: 1121-1123). Such antibody binding portions are known in the art (Kontermann and Dubel eds., Antibody Engineering (2001) Springer-Verlag. New York. p. 790 (ISBN 3-540-41354-5). Alternatively, it is also well known in the art that multivalent binding antibody variants can be generated using self-assembling units linked to the variable domain.

Bispecific, trispecific, or antibodies of multiple specificities are created by combining the heavy and light chains of one antibody with the heavy and light chains of one or more other antibodies. These chains can be covalently linked. For example, the term "bispecific antibody" refers to full-length antibodies that are generated by quadroma technology (see Milstein and Cuello (1983) Nature 305(5934): 537-40), by chemical conjugation of two different monoclonal antibodies (see Staerz et al. (1985) Nature 314(6012): 628-31), or by knob-into-hole or similar approaches which introduces mutations in the Fc region (see Holliger et al. (1993) Proc. Natl. Acad. Sci. USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). A bispecific antibody has two distinct antigen binding arms (in both specificity and CDR sequences), and is monovalent for each antigen to which it binds.

A series of murine antibodies capable of bind tau have been raised using methods known in the art. See Holtzman et al., WO2014/08404. Further, these antibodies have been screened to identify antibodies with specific biological activity that may them suitable candidates for therapeutic uses.

In one aspect, the present disclosure provides composite humanized antibodies. Composite Human Antibody™ technology generates humanized antibodies by identifying potential T cell epitopes in the variable region (V region) sequences of the donor antibody and engineering antibodies or antigen-binding fragments in such a way that binding to the potential T cell epitopes are eliminated (See EP2,388,871). Unlike other humanization technologies that use a single human light and heavy chain V region framework or human consensus framework as light and heavy chain 'acceptors' for the respective complementarity determining regions (CDRs) from the donor antibody (typically murine); Composite Human Antibodies™ comprise multiple sequence segments ("composites") derived from V regions of unrelated multiple human antibodies.

Sequence segments derived from databases of unrelated human V regions are selected after determining amino acids that are considered critical for antigen binding of the starting antibody. All selected sequence segments derived from human V region databases are filtered for the presence of potential CD4+ T cell epitopes using in silica tools known in the art. Composite Human Antibodies™ retain affinity and specificity better than standard humanized antibodies due to the close fit of human sequence segments with all sections of the starting antibody V regions. Composite Human Antibodies™ are depleted of T cell epitopes and therefore considered both humanized and de-immunized.

In one embodiment the murine variable regions from a donor antibody replace human variable regions in a human acceptor IgG resulting in a chimeric antibody.

In a further embodiment the murine CDR sequences from a donor antibody replace the CDR sequences in a human acceptor IgG, to create a humanized antibody. Further changes are incorporated into the humanized antibody to remove potential T cell epitopes and framework residues considered critical to maintaining the binding characteristics of the donor antibody. One with skill in the art will know that other methods such as CDR grafting can be used to humanize an antibody.

In a further embodiment non-human antibodies capable of binding to human tau are humanized.

The present antibodies may exhibit altered binding affinity and/or altered immunogenicity as compared to donor antibodies. In some embodiments, chimeric or humanized antibodies have substantially the same binding affinity as the donor antibody with respect to an epitope of tau.

In a further embodiment, a single-chain variable fragment based on a humanized antibody as described herein, e.g., humanized anti-tau antibody, may bind as a monomer.

In a further embodiment multivalent binding, using antibody fragments can be achieved by using diabodies, triabodies, tetrabodies, and other higher order variants, which may be prepared.

In a further embodiment the heavy and light chain of the humanized anti-tau antibody may be combined with the heavy and light chains of other antibodies to form bispecific or other additional multi specific antibodies.

Further the humanized antibodies of the invention, e.g., humanized anti-tau antibody may also be in the form of a antibody fragment, e.g., a Fab, a Fab'monomer, a F(ab)'2 dimer, or a whole immunoglobulin molecule.

In one embodiment, the invention provides an isolated peptide consisting of the amino acid sequence, DQGGYT (SEQ ID NO: 9). This peptide is a core epitope for the antibodies described herein as $C_2$N-8E12 or HJ8.5. In one aspect of the invention, the peptide includes $X_{(0-8)}$DQG-GYT$X_{(0-8)}$ (SEQ ID NO: 56) wherein X is any amino acid. While the illustrative example shows 15 mers (see FIG. 11), one of skill in the art would recognize that a peptide of different lengths are included in the invention. Accordingly, the present antibodies or fragments may specifically bind an epitope containing the amino acid sequence DQGGYT (SEQ ID NO: 9). The epitope can be a linear or conformational epitopes and can be from about 6 to 22 amino acids in length.

In other embodiments, the present methods relate to treating a tauopathy with the antibody or antigen-binding fragment, wherein the antibody or fragment is administered in a dose to a subject having a tauopathy.

Suitable doses of the antibody or antigen-binding fragment may be express in terms of mg of drug per kg of subject's body weight. Suitable doses of the antibody or antigen-binding fragment include at least about 0.1 mg/kg, alternatively about 0.2 mg/kg, alternatively about 0.25 mg/kg, alternatively about 0.3 mg/kg, alternatively about 0.5 mg/kg, alternatively about 0.75 mg/kg, alternatively about 1 mg/kg, alternatively about 1.25 mg/kg, alternatively about 1.5 mg/kg, alternatively about 2 mg/kg, alternatively about 5 mg/kg, alternatively about 7.5 mg/kg, alternatively about 10 mg/kg, alternatively about 12.5 mg/kg, alternatively about 15 mg/kg, alternatively about 20 mg/kg, alternatively about 25 mg/kg, alternatively about 30 mg/kg, alternatively about 50 mg/kg, alternatively about 100 mg/kg. Suitable doses of the antibody or antigen-binding fragment may be at most about 250 mg/kg, alternatively at most about 200 mg/kg, alternatively at most about 175 mg/kg, alternatively at most about 150 mg/kg, alternatively at most about 125 mg/kg, alternatively at most about 100 mg/kg, alternatively at most about 75 mg/kg, alternatively at most about 50 mg/kg, alternatively at most about 25 mg/kg, alternatively at most about 20 mg/kg, alternatively at most about 15 mg/kg. Any of the foregoing minima and maxima may be put together to define a range (for example, from about 0.1 mg/kg to about 250 mg/kg), so long as the minimum value of the range is lower than the maximum value of the range.

Suitable doses of the antibody or antigen-binding fragment may be express in terms of mg of drug administered to a subject. Suitable doses of the humanized antibody or antigen-binding fragment include at least about 2.5 mg, alternatively at least about 5 mg, alternatively at least about 10 mg, alternatively at least about 15 mg, alternatively at least about 20 mg, alternatively at least about 25 mg, alternatively at least about 30 mg, alternatively at least about 40 mg, alternatively at least about 50 mg, alternatively at least about 60 mg, alternatively at least about 70 mg, alternatively at least about 80 mg, alternatively at least about 90 mg, alternatively at least about 100 mg, alternatively at least about 125 mg, alternatively at least about 150 mg, alternatively at least about 175 mg, alternatively at least about 200 mg, alternatively at least about 250 mg, alternatively at least about 100 mg, alternatively at least about 125 mg, alternatively at least about 300 mg. Suitable doses of the antibody or antigen-binding fragment may be at most about 2500 mg, alternatively at most about 2000 mg, alternatively at most about 1500 mg, alternatively at most about 1000 mg, alternatively at most about 750 mg, alternatively at most about 500 mg, alternatively at most about 400 mg, alternatively at most about 300 mg, alternatively at most about 275 mg, alternatively at most about 250 mg, alternatively at most about 200 mg, alternatively at most about 150 mg. Any of the foregoing minima and maxima may be put together to define a range (for example, from about 5 mg to about 2500 mg, so long as the minimum value of the range is lower than the maximum value of the range.

$C_2N$-8E12 is a humanized recombinant IgG4 anti-human tau antibody. The IgG4 backbone of $C_2N$-8E12 contains a S241P hinge stabilizing mutation that minimizes the formation of half-antibodies. $C_2N$-8E12 binds to amino acids 25-30 in human tau (DQGGYT) (SEQ ID NO: 9), a sequence that is present in all human tau splice variants as well as in amino-terminal fragments of tau. The antibody binds to both monomeric tau and aggregated tau in human brain tissue from tauopathies. $C_2N$-8E12 is highly stable with very little aggregation or degradation. General physical properties of $C_2N$-8E12 are listed in Table 1.

TABLE 1

| | |
|---|---|
| Molecular weight | 145.72 kDa |
| Stereochemistry | L-amino acids |
| Appearance | Clear, colorless to light yellow liquid |
| Solubility | ~130 mg/mL |

Although the invention has been described with reference to the attached examples, it will be understood that modifications and variations are encompassed within the spirit and scope of the invention. The attachments here are illustrative examples of the invention and herein incorporated by reference in their entirety.

Example 1

This example describes efforts and results for humanization of the murine anti-tau antibody HJ8.5. The efforts yielded four humanized light chain variable regions (VL or VK) and four humanized heavy chain variable regions (VH).

Humanization generally refers to techniques of reducing the potential immunogenicity associated with using a non-human monoclonal antibody for chronic treatment. Two methods typically used to reduce immunogenicity are CDR grafting and de-immunization. Murine antibody HJ8.5 was de-immunized using a method developed by Antitope.

CDR grafting is a protein engineering approach. Briefly, it relies on both an understanding of the basic architecture of an antibody and its conservation across species. Murine and human antibodies share a common/conserved architecture. Antibody structure is divided into constant and variable regions. The variable region can be further divided into so called framework regions and CDR regions. It can be seen that the variable region is composed of four frameworks (Fwk) and three CDR. The arrangement of frameworks and CDRs are the same in light and heavy variable domains.

In CDR grafting, the non-human constant regions are replaced with human constant regions, giving rise to a so called chimeric antibody. In addition, the murine CDR regions are transferred into human framework regions; the resulting variable domain is a mix of human frameworks and murine CDR's. As a final step, a number of the murine framework residues, thought to play a critical role in maintaining the affinity are transferred (not shown).

De-immunisation: Composite Human Antibody™ technology from Antitope is said to be a deimmunization technology that is used in conjunction with identifying both CDRs and key amino acids in the framework thought to play a role in binding. The resulting fully-humanized antibodies retain the binding affinity and specificity of the starting monoclonal antibody and are also devoid of CD4+ T cell epitopes, which avoids undesirable immunogenicity in humans.

Composite Human Antibodies™ are generated by combining multiple segments of human antibody sequences from Antitope's database comprising 100,000's of unrelated fully-human antibody variable region sequences. Initial modeling of variable region sequences of HJ8.5 antibody is used to identify amino acids critical to antibody binding, which are then used to constrain the selection of human sequence segments. Individual sequence segments and the junctions between adjacent segments are then analyzed using two proprietary in silico technologies (iTope™ and TCED™) for selection of fully-human variable region sequences that are devoid of CD4+ T cell epitopes. DNA encoding variable regions for Composite Human Antibodies are synthesized, cloned onto an expression vector with human constant regions and transfected into mammalian cells for production of the humanized antibodies.

Humanization of HJ8.5: Structural models of the HJ8.5 murine anti-Tau412 antibody V regions were produced using Swiss PDB and analyzed in order to identify important "constraining" amino acids in the V regions that were likely to be essential for the binding properties of the antibody. From the analysis, a number of constraining framework residues were identified as candidates for inclusion in the fully humanized V regions. Segments of human variable region sequences were selected to include one or more of these residues.

A preliminary set of human sequence segments that could be used to create the fully humanized HJ8.5 antibodies were selected and analyzed using iTope™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that were identified as significant non-human germline binders to human MHC class II or that scored significant hits against the TCED™ were discarded. Combinations of sequence segments were also analyzed to ensure that the junctions between segments did not contain potential T cell epitopes. Selected segments were then combined to produce heavy and light chain V region sequences for synthesis. For HJ8.5, four VH chains and four VK chains were designed and constructed.

FIG. 1 shows the variable region sequences of the murine HJ8.5 antibody as well as 4 humanized variant sequences for each of the heavy and light chains (4 VH and 4 VL/VK sequences). The amino acid sequences of those four VH chains and four VK chains are set forth in FIG. 1. The CDR sequences, as defined by Kabat et al are highlighted in red (underlined). Framework changes from the original mouse sequence are highlighted in blue and in bold.

Table B-1 summarizes the number of framework changes introduced in each variant of the heavy and light chain variable domains.

TABLE B-1

| Variable Domain | Number of Framework changes |
| --- | --- |
| VH1 | 4 |
| VH2 | 5 |
| VH3 | 10 |
| VH4 | 11 |
| VK1 | 6 |
| VK2 | 7 |
| Vk3 | 11 |
| VK4 | 12 |

FIG. 2 shows the sequences of the humanized variable and constant region sequences for each of the heavy and light chains (4 VH and 4 VL/VK sequences). The variable heavy chain is grafted to the constant heavy chain of human IgG4 containing the S241P hinge stabilizing mutation. The variable light chain is grafted to the constant light chain of human Kappa light chain. This table also lists the theoretical isoelectric point (PI) and molecular weight (Mw).

FIG. 3 shows expression data from 2 rounds of transient expression of cells transfected with polynucleotides encoding VH and VK regions. Results for 13 humanized anti tau antibodies are summarized. Different combinations of heavy and light chains resulted in markedly different levels of expression being observed. In Round 1, all variants of VH and VL regions were combined with each other (only results for 13 are shown of the 16 that were tested. In Round 2, the 6 best expressing combinations observed in Round 1 were tested. Expression is shown as µg of antibody measured per mL of culture media. Higher levels of expression is advantageous since it suggests that the antibody is correctly folded, secreted as expected, non toxic and generally stable.

FIG. 4 shows data from a potency assay. To further characterize the humanized anti-tau antibody variants, the potency assay evaluates the ability of antibodies to compete with the original murine HJ8.5 (parent antibody) for binding to human tau in an ELISA type format. The assay format involves coating the ELISA plate with human tau and then allowing the test antibodies as well as biotinylated HJ8.5 to compete for binding to tau. The assay enables the relative IC50 value for each humanized antibody variant to be measured. IC50 values are normalized to that of chimeric HJ8.5 to enable comparisons to be made between plates. This data demonstrates that the humanization process has not significantly changed the binding of the humanized antibodies to human tau.

Example 2

This study describes the use of the Biacore T200 to measure and compare the binding characteristics of the interaction between six fully humanized (VH1/VK2, VH1/VK3, VH2/VK2, VH2/VK3, VH3/VK2 and VH3/VK3, described above in Example 1) monoclonal antibodies and one chimeric monoclonal antibody based on HJ8.5 with recombinant human Tau-412 protein. The aim of this study was to use the Biacore T200 surface plasmon resonance instrument for the high resolution kinetic characterization of the interactions between Tau-412 and these seven mAbs.

The antibodies were stored at 4° C. Tau-412 was stored at −20° C. as per the manufacturer's instructions. Once reconstituted the Tau-412 solution was stored on ice and used within 24 hours. Aliquots of reconstituted Tau-412 were frozen within 30 minutes of reconstitution and stored at −20° C.

The Biacore instrument was run on Biacore T200 Evaluation Software V1.1 (Uppsala, Sweden). All materials were from Biacore unless stated:

| | |
| --- | --- |
| Biacore Preventative Maintenance Kit 2 | BR-1006-51 |
| Series S CM5 Sensor Chips | BR-1006-68 |
| Amine Coupling Kit | BR-1000-50 |
| 10 mM Acetate pH 4.5 | BR-1003-51 |
| HBS-EP Running buffer\ | BR-1006-69 |
| 10 mM Glycine-HCl pH 1.5 | BR-1003-54 |
| 10 mM Glycine-HCl pH 2.0 | BR-1003-55 |
| Protein A (Sigma) | P6031 |
| 4M MgCl$_2$ hexahydrate (Sigma) | M9272-500G |

All experiments were developed with Biacore 'wizard' software. The following Biacore methods were used: Immobilization; Kinetics/Affinity; and Desorb and Sanitize.

Before running any samples, and during the study, a system check (Biacore Preventative Maintenance Kit 2) was performed. All the systems tested passed (Reagent pump, Refractometer, Injections, Noise, Mixing and Buffer Selector) indicating that the instrument was performing to criteria set by the manufacturer.

Upon insertion of a CM5/Protein A chip the system was primed and then normalized with BIA normalizing solution (Biacore Preventative Maintenance Kit 2). All samples were run at 25° C. with a sample rack incubated at 5° C. The chip was added to the system with HBS-EP used as the running buffer.

The mAbs were stored as supplied and diluted to 100 nM for all immobilization (capture) runs. The antigen Tau-412 was reconstituted from the dry powder using Milli-Q water to a final concentration of 1 mg/mL; further dilutions were performed for the kinetics runs. The mass and molecular weight of Tau-412 used in the concentration calculation was provided by the reagent manufacture (100 µg/vial and 42.9 kDa). No carrier protein was added to this solution. Vials of the antigen were only reconstituted when required and were stored in their powder form at −20° C. until use. Once reconstituted, the antigen solution was kept on ice and used within 24 hours.

A capture assay with protein A was selected for this study. The performance of the Protein A surface was superior to the anti-human, protein A/G, protein G and protein L surfaces that were also tested. The Protein A chip was prepared through immobilization using standard amine coupling chemistry. Immobilization was carried out at a protein concentration of 5 µg/mL in 10 mM Acetate buffer pH 4.5 to a target response level of 500 RUs on a CM5 Series S sensor chip (Biacore).

The final response levels for the Protein A chip 'All' and designated F$_c$s are shown in Table G-1.

TABLE G-1

| | Ligand | Final Response Level (RU) |
|---|---|---|
| Fc1 | Protein A | 697.1 |
| Fc2 | Protein A | 691.4 |
| Fc3 | Protein A | 708.3 |
| Fc4 | Protein A | 704.6 |

For kinetic experiments, the amount of immobilized/captured ligand needs to be limited to avoid mass transfer effects at the surface of the chip. For kinetic experiments, a surface should ideally have a maximum analyte binding level ($R_{max}$) of 50-100 RUs. The amount of ligand to immobilize is therefore calculated using Equation 1:

$$\text{analyte binding capacity } (RU) = \frac{analyteMW}{ligandMW} \cdot \text{immobilized ligand } (RU) \cdot Sm$$

Using an average MW of 42.9 kDa (provided by the reagent manufacture) for the analyte Tau-412, 150 kDa for the ligand (estimated value for antibodies) (mAb), 100 RU for $R_{max}$, and the stoichiometry ($S_m$) as 1, a target of 300 RUs was set for capture of all the trial antibodies. The capture levels obtained within the study varied from ~280-400 RU's. For the second and third runs the amount of injected antibody was adjusted to get closer to the desired 300 RU capture level.

Non-specific binding can be due to either the analyte or analyte contaminants interacting with either the ligand (non-specific and difficult to detect), capture protein, or the sensor chip surface. By analyzing the response of the blank $F_c1$ surface after a relatively high concentration (40 nM) 300 second injection of Tau-412, no NSB was observed to the carboxy-dextran surface, or Protein A capture surface. At Tau-412 concentrations>100 nM, significant NSB was observed to the carboxy-dextran chip surface; however concentrations within this range were not required for subsequent kinetic analysis.

Regeneration scouting was performed and the optimum conditions for the regeneration of chimeric and VH1/VK2 antibodies on the Protein A surface were as follows. Three 240 second injections of 10 mM Glycine-HCl pH 1.7 followed by one 300 second injection of 4M MgCl$_2$ all at 40 µL/min. A 600 second wait step was introduced after the last regeneration injection to allow the surface to stabilize before starting the next binding cycle.

No buffer scouting was performed as initial tests indicated the selected buffer 'HBS-EP' generated a reproducible system suitable for kinetic analysis.

The performance of the surface was analyzed by repeated control injections of 2.5 nM Tau-412 at the start, interspaced and at the end of a kinetic run. Stable binding was observed throughout the kinetic run highlighting the suitability of the system for kinetic analysis.

Mass transport limitation occurs when the rate of association contains a significant component associated with the rate of transport of the analyte to and from the chip surface. Where mass transfer is found to be significant the resulting kinetic analysis could be inaccurate. Lowering the density of immobilized ligand, or increasing the flow rate, can reduce mass transport limitations. From previous experience of using low density surfaces and similar Mw antigens, a flow rate of 40 µL/min was selected for this study.

The linked reaction control experiment is used to assess the ligand-analyte interaction to check for deviations from a 1-to-1 binding model. The analyte is injected over the surface for different periods of time (contact times) and the dissociation rate is analyzed to determine if it varies with the contact time. If such a relationship is observed, it indicates that a second interaction event is taking place after the initial binding event that results in a stabilized complex at the surface.

From previous experience using capture assay formats, the apparent binding stoichiometry of 1.5 and that a 1-to-1 model could be fitted with confidence to the resulting kinetic data, linked reaction controls were not performed as there was no additional evidence to support more complex kinetic interactions.

A 1-to-1 binding model was used to fit the resulting kinetic data (Equation 2). Due to variations in the amount of antibody captured the parameter $R_{max}$ was set to local as opposed to global analysis for each antibody kinetic analysis.

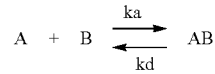

Antibody Characterization: The characterization and the control experiments performed for the Protein A capture surface suggested this was a suitable system to determine kinetic values for the Tau-412 interactions. The binding stoichiometry was assessed by injecting a saturating concentration of Tau-412 (1000 nM) over 277 RU's of captured VH1/VK2 on a trial Protein A surface. Two sequential injections of 1000 nM Tau-412 appeared to result in saturated binding at 122 RU's. This resulted in a binding stoichiometry of 150%, which is higher than expected for one antibody molecule binding to one Tau-412 molecule. Reasons for this could include binding of the antibody to two molecules of Tau-412 or Tau-412 oligomerization on the surface of the chip.

Kinetic data was obtained at a flow rate of 40 µL/min to minimize any potential mass transfer effects. Two repeats of the blank (no antigen) and the 2.5 nM concentration of the analyte were programmed into the kinetic run in order to check the stability of both the surface and analyte over the kinetic cycles. For the initial kinetic runs, 2-fold dilutions of Tau-412 from 40 nM to 0.156 nM were run. For kinetic analysis and on subsequent runs, an analyte range of 20 nM to 0.625 nM was selected. This range covered multiple analyte concentrations both above and below the reported $K_D$.

The association phase was monitored for 500 seconds to allow some of the higher concentrations of analyte to reach steady state. In order to observe a sufficient signal decrease (>10%) during the dissociation phase of the kinetic cycle, dissociation was measured for 1200 seconds. As discussed in Section 5, the $F_c$s were allowed to stabilize for 600 seconds after each regeneration step. The signal from the reference channel $F_c1$ was subtracted from that of $F_c2$, $F_c3$ and $F_c4$.

The kinetic parameters for the interaction of Tau-412 with the 7 mAbs as measured using the Protein A capture system on the Biacore T200 are shown in Table F-2. To correct for differences in the capture level of the antibody between each binding cycle, a local $R_{max}$ parameter was used in the 1-to-1 binding model. Kinetic analysis was performed in three independent runs using fresh preparations of Tau-412 and antibody. Run 1 and runs 2+3 used different vials of the antigen Tau-412; therefore the reported errors associated with the mean response probably represent variation in preparation of the analyte and differences in assay set-up and run. From run 1 to runs 2+3, the amount of antibody injected was adjusted to try to get closer to the target 300 RU capture levels. For run 1, the chimeric antibody was run in triplicate and an analysis of all three data sets is shown in Table F-2. The % CV for the $K_D$ derived from these three data sets was 4.3% indicating that the results were within assay variability.

antibodies have very similar affinities and that differences are purely a result of assay variation. In general, the differences in binding between the antibodies may be attributable to assay variation, and it is believed there are no significant differences in KD values of the humanized antibodies compared to the chimeric antibody.

A comparison of the kinetic values determined using the protein A capture assay on the Biacore T200 for the interaction between the antibodies and Tau-412 are shown. The chimeric antibody appears to display a significantly different binding profile when compared to the humanized antibodies,

TABLE F-2

| Ligand | Chip | $k_a$ (1/Ms) | SE($k_a$) | $k_d$ (1/s) | SE($k_d$) | $K_D$ (nM) | SD ($K_d$) | Chi² | Appendix II |
|---|---|---|---|---|---|---|---|---|---|
| VH1/VK2 | A11/1 | $2.80 \times 10^5$ | $4.40 \times 10^2$ | $6.11 \times 10^{-4}$ | $2.80 \times 10^{-7}$ | 2.18 | | 1.28 | A3-4 |
| VH1/VK2 | A11/3 | $3.25 \times 10^5$ | $1.00 \times 10^3$ | $6.32 \times 10^{-4}$ | $8.20 \times 10^{-7}$ | 1.95 | | 0.44 | A5-6 |
| | | $k_a$ (1/Ms) | SE($k_a$) | $k_d$ (1/s) | SE($k_d$) | $K_D$ (nM) | SD($K_D$) (nM) | | |
| Mean | | $3.02 \times 10$ | $3.19 \times 10^4$ | $6.21 \times 10^{-4}$ | $1.48 \times 10^{-5}$ | 2.05 | 0.17 | | |
| Ligand | Chip | $k_a$ (1/Ms) | SE($k_a$) | $k_d$ (1/s) | SE($k_d$) | $K_D$ (nM) | SD (KD) | Chi² | Appendix II |
| VH1/VK3 | A11/1 | $2.80 \times 10^5$ | $9.10 \times 10^2$ | $6.26 \times 10^{-4}$ | $8.50 \times 10^{-7}$ | 2.24 | | 0.99 | A7-8 |
| VH1/VK3 | A11/2 | $2.95 \times 10^5$ | $4.40 \times 10^2$ | $5.72 \times 10^{-4}$ | $2.70 \times 10^{-7}$ | 1.94 | | 0.52 | A9-10 |
| | | $k_a$ (1/Ms) | SE($k_a$) | $k_d$ (1/s) | SE($k_d$) | $K_D$ (nM) | SD($K_D$) (nM) | | |
| Mean | | $2.87 \times 10^5$ | $1.07 \times 10^4$ | $5.99 \times 10^{-4}$ | $3.76 \times 10^{-5}$ | 2.09 | 0.21 | | |
| VH2/VK2 | A11/1 | $2.62 \times 10^5$ | $4.30 \times 10^2$ | $6.28 \times 10^{-4}$ | $2.80 \times 10^{-7}$ | 2.40 | | 0.83 | A11-12 |
| VH2/VK2 | A11/2 | $2.84 \times 10^5$ | $4.10 \times 10^2$ | $5.87 \times 10^{-4}$ | $2.60 \times 10^{-7}$ | 2.06 | | 0.70 | A13-14 |
| | | $k_a$ (1/Ms) | SE($k_a$) | $k_d$ (1/s) | SE($k_d$) | $K_D$ (nM) | SD($K_D$) (nM) | | |
| Mean | | $2.73 \times 10^5$ | $1.59 \times 10^4$ | $6.08 \times 10^{-4}$ | $2.94 \times 10^{-5}$ | 2.23 | 0.24 | | |
| VH2/VK3 | A11/1 | $2.68 \times 10^5$ | $8.80 \times 10^2$ | $6.53 \times 10^{-4}$ | $9.00 \times 10^{-7}$ | 2.44 | | 1.11 | A15-16 |
| VH2/VK3 | A11/2 | $2.92 \times 10^5$ | $4.40 \times 10^2$ | $5.33 \times 10^{-4}$ | $2.60 \times 10^{-7}$ | 1.83 | | 0.50 | A17-18 |
| | | $k_a$ (1/Ms) | SE($k_a$) | $k_d$ (1/s) | SE($k_d$) | $K_D$ (nM) | SD($K_D$) (nM) | | |
| Mean | | $2.80 \times 10^5$ | $1.71 \times 10^4$ | $5.93 \times 10^{-4}$ | $8.44 \times 10^{-5}$ | 2.13 | 0.43 | | |
| VH3/VK2 | A11/1 | $2.62 \times 10^5$ | $3.20 \times 10^2$ | $5.46 \times 10^{-4}$ | $2.20 \times 10^{-7}$ | 2.08 | | 0.45 | A19-20 |
| VH3/VK2 | A11/2 | $2.90 \times 10^5$ | $3.70 \times 10^2$ | $4.85 \times 10^{-4}$ | $2.20 \times 10^{-7}$ | 1.67 | | 0.71 | A21-22 |
| | | $k_a$ (1/Ms) | SE($k_a$) | $k_d$ (1/s) | SE($k_d$) | $K_D$ (nM) | SD($K_D$) (nM) | | |
| Mean | | $2.76 \times 10^5$ | $1.99 \times 10^4$ | $5.15 \times 10^{-4}$ | $4.28 \times 10^{-5}$ | 1.88 | 0.29 | | |
| VH3/VK3 | A11/1 | $2.54 \times 10^5$ | $3.10 \times 10^2$ | $5.59 \times 10^{-4}$ | $2.00 \times 10^{-7}$ | 2.20 | | 0.80 | A23-24 |
| VH3/VK3 | A11/2 | $2.76 \times 10^5$ | $3.80 \times 10^2$ | $4.54 \times 10^{-4}$ | $2.20 \times 10^{-7}$ | 1.65 | | 0.80 | A25-26 |
| | | $k_a$ (1/Ms) | SE($k_a$) | $k_d$ (1/s) | SE($k_d$) | $K_D$ (nM) | SD($K_D$) (nM) | | |
| Mean | | $2.65 \times 10^5$ | $1.56 \times 10^4$ | $5.07 \times 10^{-4}$ | $7.40 \times 10^{-5}$ | 1.92 | 0.39 | | |
| Chimeric | A11/1 | $7.18 \times 10^5$ | $1.60 \times 10^3$ | $1.60 \times 10^{-3}$ | $2.40 \times 10^{-5}$ | 2.23 | | 1.17 | A27-29 |
| Chimeric | A11/2 | $7.22 \times 10^5$ | $3.00 \times 10^3$ | $1.30 \times 10^{-3}$ | $3.50 \times 10^{-5}$ | 1.79 | | 0.97 | A30-31 |
| Chimeric | A11/3 | $7.23 \times 10^5$ | $2.60 \times 10^3$ | $1.40 \times 10^{-3}$ | $3.30 \times 10^{-5}$ | 1.94 | | 0.49 | A32-33 |
| | | $k_a$ (1/Ms) | SE($k_a$) | $k_d$ (1/s) | SD($k_d$) | $K_D$ (nM) | SD($K_D$) (nM) | | |
| Mean | | $7.21 \times 10^5$ | $2.87 \times 10^3$ | $1.43 \times 10^{-4}$ | $1.54 \times 10^{-4}$ | 1.99 | 0.22 | | |

The Chi² values show how well the association and dissociation data fits the proposed 1-to-1 binding model—the lower the value the better the fit. The associated SE values for the rate constants represent the uncertainty associated with fitting the data to the model described, and do not represent the total uncertainty for the true kinetic values. The mean response data represents the average kinetic values and the associated SD from 2, or 3 independent analyses.

Using the mean $K_D$ values from Table F-2, the antibodies can be ranked based on affinity as follows: VH3/VK2>VH3/VK3>Chimeric>VH2/VK3>VH/VK3>VH1/VK2>VH2/VK2. The % CV associated with the mean kinetic parameters ranged from 10-20%, and thus it is likely that all although the affinities are similar. A $k_d$ versus $k_a$ plot shows the relative kinetic values of the tested antibodies and Tau-412 interactions as determined using the Protein A capture assay on the Biacore T200. The dashed diagonals represent isoaffinity lines. Please note the axes display different data ranges, with the aim of improving the clarity of the humanized antibodies on the plot.

FIG. 5 summarizes the results from surface plasmon resonance (SPR) analysis, determining the binding kinetics of the 6 best expressing humanized constructs against human tau. The test antibody is immobilized on the SPR chip with different concentrations of human tau then allowed to flow over the chip. Association and dissociation rates as well as the affinity based on the measured binding events is calculated for each of the variants. The chimeric variant was also tested.

Example 3

FIG. 6 shows the binding of four humanized antibody variants to soluble human tau in a sandwich style ELISA. Assay methods that rely on passive adsorption have the potential to create artifactual binding results. To overcome this possibility, a solution based method to measure the binding activity of the humanized antibody variants was employed. In this assay format, antigen (human tau) is captured by a monoclonal anti-human tau antibody that recognizes a different epitope than HJ8.5. Subsequent binding of the humanized anti-tau antibodies to the captured human tau depends on antigen concentration, while IgG4 isotype controls shows no binding at all. This assay demonstrates that binding of the humanized anti-tau antibodies to human tau is specific and that the antibodies bind to soluble human tau.

Example 4

FIGS. 7A-7MM show binding of humanized and control antibodies to tissue from wild type mice (negative control tissue), P301S mice (which express human tau having a P301S mutation and develop age associated tau pathology), and humans with either Alzheimer's disease or Progressive Supranuclear Palsy (PSP). The aim of this study was to confirm that humanized antibodies retain the ability to bind to aggregated tau in tissue as compared to the chimeric form of HJ8.5. The figures show representative images of staining human and mouse brains with different variants of humanized HJ8.5 antibody. P301S mice at 4 and 9 month old were tested, and both time points show pathologic aggregates of tau, with the 9 month old mice having more tau pathology than the 4 month old mice. For human staining, a sample of brain tissue from one subject with PSP, and a sample of brain tissue from one subject with AD was examined. FIGS. 7A-7E illustrate staining with chimeric HJ8.5 for the mouse and human AD tissue. FIGS. 7F-7I illustrate the staining with a negative control antibody (non-specific human IgG4). FIGS. 7J-7MM illustrate the staining with the six humanized antibodies. All humanized variants of the murine HJ8.5 antibody bind to tau aggregates found in P301S mouse brain as well as tau aggregates found in the brain tissue of the subjects diagnosed with either AD or PSP.

Example 5

Figure 8:
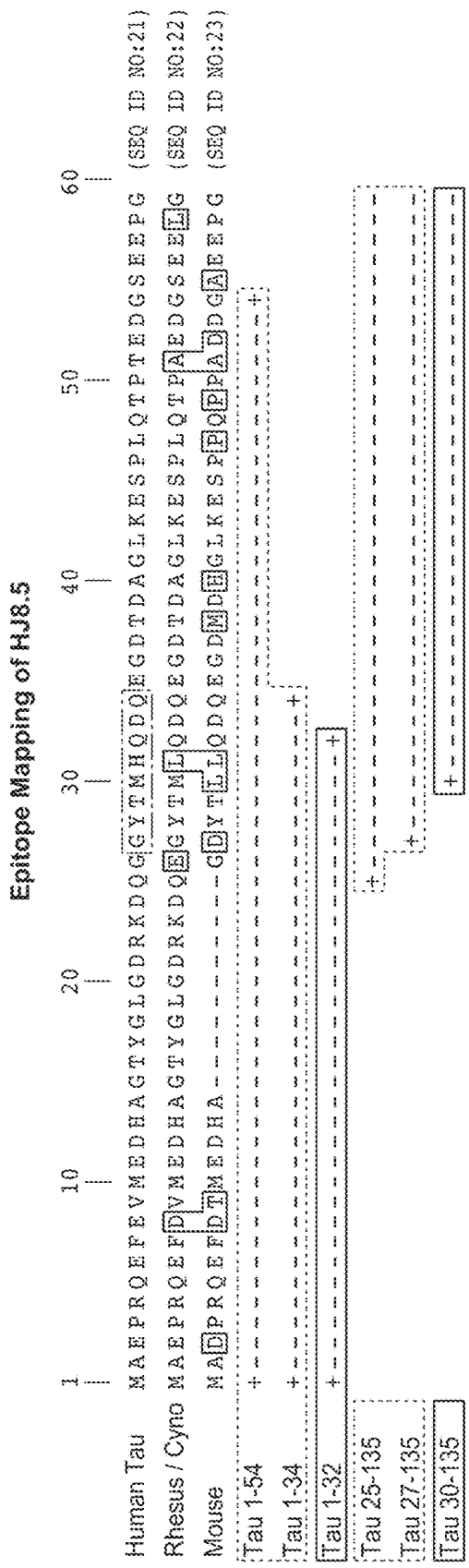
FIG. 8 shows the epitope mapping for the murine antibody HJ8.5 against the amino acid sequence of human tau.

FIG. 8 shows the epitopes of HJ8.5 in human tau. The epitope was mapped using yeast display. For this method, various peptides covering the sequence of human tau were expressed using by yeast. Binding of the HJ8.5 antibody to yeast in culture was measured by immunofluorescence. Binding to yeast, expressing variants of tau that included the first 34 amino acids was observed, but no binding, if the yeast only expressed the first 32 amino acids of tau. This suggests that the epitope is within the first 34 amino acids. Additionally, HJ8.5 binds if the peptide includes amino acids 27-135 but not if the peptide spans amino acids 30-135. This suggests that the epitope includes amino acids greater than amino acid 27. Based on this data the epitope is contained within the 27-34 sequence of human tau (GYT-MHQDQ (SEQ ID NO: 10). FIG. 8 also shows the rhesus monkey and mouse tau sequences and highlights in red the amino acid changes from human tau.

FIG. 9 shows more detailed, peptide-based epitope mapping of HJ8.5 and $C_2$N-8E12. A peptide library of linear 15mers spanning the full sequence of human tau (1N4R, 412 amino acids) was created. Additionally double alanine versions of these peptides where amino acids 10 and 11 were changed to alanine were also produced. For the double alanine library, any naturally occurring alanines at position 10 or 11 were mutated to glycine. All peptides were spotted onto a peptide array and then probed with HJ8.5 or $C_2$N-8E12 and binding measured. The tau binding epitope(s) of both antibodies were reliably mapped using these peptide arrays. The binding epitope of $C_2$N-8E12 is $_{25}$DQGGYT$_{30}$ (SEQ ID NO: 9) and matches the epitope of the murine parent, HJ8.5. The binding of HJ8.5 and $C_2$N-8E12 to tau peptides is severely compromised when amino acids D, Q, Y, or T in the epitope were replaced with alanine, suggesting that they play a crucial rule in the antibody binding. However, when the central two glycines in the epitope were replaced with alanine, the binding of antibodies to the tau peptides was not as severely compromised (PEP 2875811). This is likely not an indication that these amino acids are not important for binding but rather due to the conservative nature of substitutions between Alanine and Glycine amino acids. The epitope mapped using these more detailed methods is slightly different from what was mapped using yeast display (FIG. 8). This difference is attributed to the difference in the binding assays, with larger peptides being used on the yeast display system. The 15mer peptide array methodology is considered to be superior to the yeast display methodology.

Example 6

Figure 10:
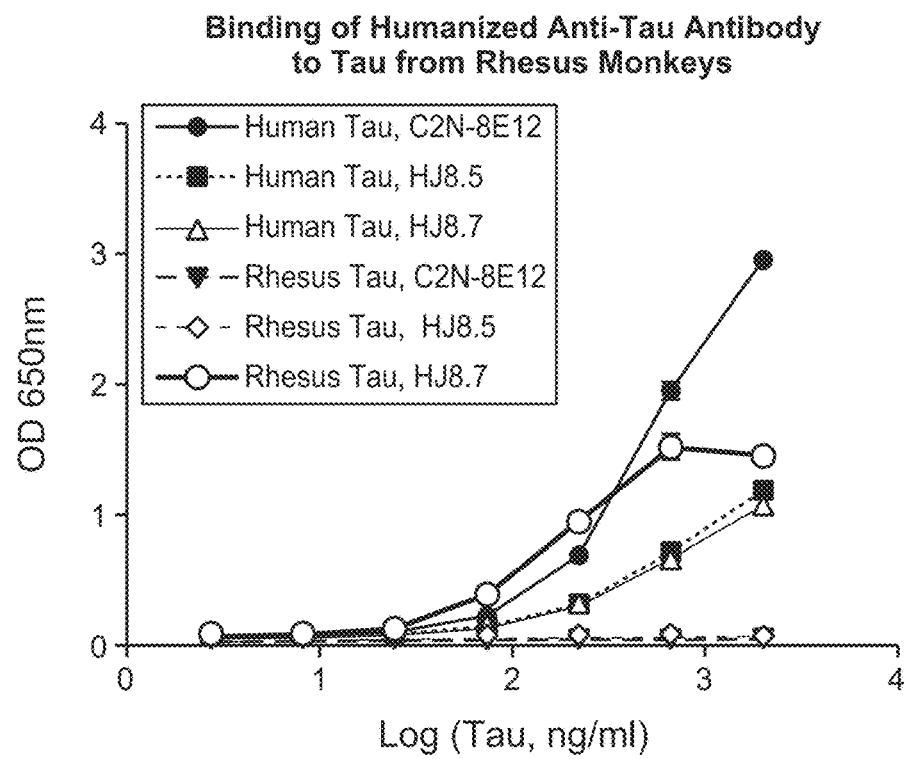
FIG. 10 illustrates the binding results for different anti human tau antibodies to either human or rhesus monkey tau. The results demonstrate that $C_2$N-8E12 and HJ8.5 do not bind to rhesus tau while they do show positive binding to human tau. HJ8.7 binds to both human and rhesus tau.

FIG. 10 illustrates the binding results for different anti human tau antibodies to either human or rhesus monkey tau. Murine anti human tau antibodies HJ8.5 and HJ8.7 alongside humanized variant VH1/VK2 (also referred to as $C_2$N-8E12) were tested. FIG. 8 shows that there is a single amino acid difference at position 32 between human and rhesus tau, in the claimed binding epitope sequence GYTM(H/L)QDQ (SEQ ID NO: 57). FIG. 8 shows that there is a single amino acid difference at position 27 between human and rhesus tau, in the claimed binding epitope sequence DQ(G/E)GYT (SEQ ID NO: 58). In order to determine whether these amino acid difference between the two species of tau, impacts the ability of antibodies HJ8.5/$C_2$N-8E12 to bind the following experiment was performed. Binding of $C_2$N-8E12, HJ8.5 (murine precursor of $C_2$N-8E12), and HJ8.7 (murine anti-human tau antibody that binds to an epitope of tau where the human and rhesus amino acid sequence is 100% conserved) to human and rhesus tau by coating 96 well ELISA plates with either human or rhesus tau at various concentrations was measured. Our results demonstrated that $C_2$N-8E12 and HJ8.5 do not bind to rhesus tau while they do show positive binding to human tau. As expected, HJ8.7 binds to both human and rhesus tau.

Example 7

Figure 11:
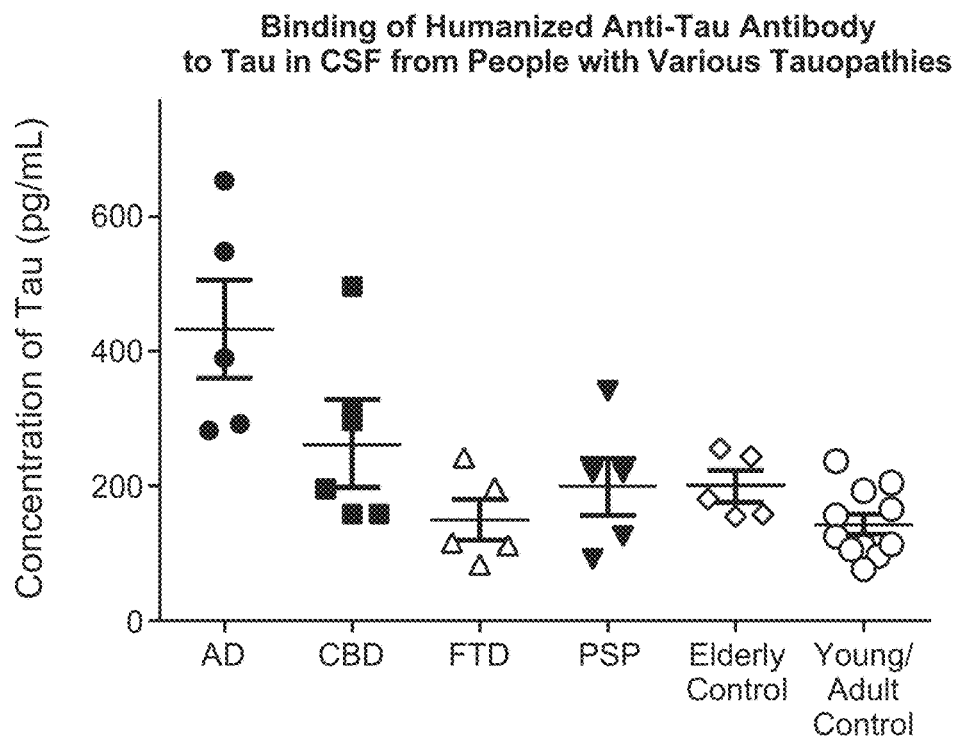
FIG. 11 shows binding of humanized anti-tau antibody to tau in CSF from human subjects with various tauopathies. The binding of $C_2$N-8E12 to tau in CSF samples from subjects diagnosed with a variety of tauopathies was evaluated.

FIG. 11 shows binding of humanized anti-tau antibody to tau in CSF from human subjects with various tauopathies. The binding of $C_2$N-8E12 to tau in CSF samples from subjects diagnosed with a variety of tauopathies as well as age matched and young normal control subjects was evaluated. A sandwich ELISA was used to demonstrate binding of C$_2$N-8E12 to tau in human CSF from subjects with AD, CBD, FTD, or PSP as well as age matched and young/adult controls. C$_2$N-8E12 was used as the coating antibody to capture tau in CSF samples. Biotinylated murine monoclonal tau antibody HJ8.7 was used as the detection antibody. Wells coated with control human IgG4 acted as the negative control for the experiments. A big difference in signal from C$_2$N-8E12 coated wells vs. control IgG4 coated wells was observed, demonstrating specific binding of C$_2$N-8E12 to tau in human CSF samples. By including a standard curve (recombinant tau), it is possible to get quantitative information on tau concentration in these CSF samples.

Example 8

This study is a randomized, double blind, placebo controlled, single ascending dose (SAD) phase 1 study to be conducted in up to ten (10) centers. It is designed to evaluate the safety, tolerability, immunogenicity, and PK of single-dose administration of C$_2$N-8E12 and to establish the MTD to be used in future repeat dosing studies.

The primary objective of this study is to determine the safety, tolerability, immunogenicity, and maximally tolerated dose (MTD) of a single dose of C$_2$N-8E12 in subjects with PSP. Safety assessments will include physical and neurologic examination, clinical safety laboratory studies, immunogenicity, adverse events, vital signs and concomitant medication review.

The secondary objectives are to determine: Single-dose systemic pharmacokinetics including; Maximum plasma concentration after single infusion; Area under the curve (AUC) after single infusion; Time at which the maximum concentration after infusion is achieved; Terminal half-life of C$_2$N-8E12; Partition of C2N-8E12 into cerebrospinal fluid (CSF); and Biologic target engagement through the measurement of soluble tau levels in blood and CSF as well as assessing the presence of C$_2$N-8E12-tau complexes.

This study intends to enroll 32 subjects with PSP (24 in the treatment arm and 8 in the placebo arm). Subjects will be enrolled in 8 blocks of 4 patients, with one patient in each block randomized to placebo and 3 to the current estimate of the MTD. Additional subjects may be enrolled if DLTs occur. No dose may be skipped, however, during the dose escalation process.

A continual reassessment method (CRM) for dose escalation will be used as described in the statistical design section. A logistic model will be used to identify the probability of DLT by dose.

C$_2$N-8E12 will be shipped to the clinical site as a frozen liquid in single use bottles at a nominal concentration of 20 mg/mL. Each bottle contains 300 mg C$_2$N-8E12 and must be stored frozen at −70° C. to −80° C.

Patients will undergo screening to assess whether inclusion and exclusion criteria are met. Screening will also include assessments of blood and CSF, and MRI. On the day of dosing (Day 0), a single dose of C$_2$N-8E12 will be administered through an IV line and subjects will be closely monitored at a clinical facility for 24 hours after dose administration. This includes blood samples for safety and PK assessments. During the following 3 days, as well as at one and two weeks after the infusion, additional clinical examination and blood sampling will occur. An additional safety MRI and CSF sampling will be performed 4 days post-infusion. Subjects will be followed every 28 days, for no less than two months from the date of dosing (e.g., day 56). Monthly measurements, thereafter, will continue until the earlier occurrence of any of the following events: (i) C$_2$N-8E12 is no longer detectable in blood; (ii) the Sponsor determines completion of the study; (iii) the subject decides to early discontinue participation in the study.

The goal of phase 1 study includes establishment of an MTD as assessed by safety evaluations including clinical laboratory tests, physical and neurologic examinations, and occurrences of adverse events to determine a recommended range of doses for evaluation in the subsequent phase 2/MAD study. Random assignment of subjects and inclusion of a placebo arm avoids bias and increases the likelihood that both known and unknown risk factors are distributed evenly between treatment groups.

A data safety monitoring committee (DSMC) will review safety data on an ongoing basis. The safety monitoring committee will be minimally comprised of two independent physicians, one biostatistician, one physician with expertise in PSP, and one non-voting member from the Sponsor. If any individual study subject experiences SAEs, all available safety data for the subject will be reviewed to determine if the event meets the definition of DLT, and whether the MTD has been established. If MTD has not been established, and patient enrollment continues, the DSMC will provide recommendations to the Sponsor whether any further actions or protocol amendments are necessary to ensure the safety of subsequently enrolled patients. The Sponsor will make final determinations on any amendments to or preliminary termination of the study.

A dose limiting toxicity is defined as: (i) any Grade 3 or higher AE per Rheumatology Common Toxicity Criteria v2 for which there is reasonable possibility that C$_2$N-8E12 caused the event; (ii) any Grade 2 AE in the NCI's Common Terminology Criteria for Adverse Events v4.0. (CTCAE) system organ class of nervous system and psychiatric disorders that is considered clinically significant and for which there is reasonable possibility that C$_2$N-8E12 caused the event; or (iii) any infusion-related toxicities (e.g., allergic reaction/hypersensitivity) occurring during the infusion of C$_2$N-8EI2 or within 24 hours after completing the infusion that do not resolve promptly with a reduced infusion rate and/or supportive care.

Dose Escalation: The assignment of subjects to dose cohorts is governed by the following rules: (1) Within each block of 4 patients, 1 patient will be allocated to the placebo arm; (2) Complete toxicity information is required for at least 3 patients at a dose level before escalation to a higher dose level; (3) The maximum increment of escalation from one cohort to the next is 1 dose level; and (4) At least 12 subjects (3 blocks) should be dosed at the MTD dose level.

Within each 4-patient cohort, patients will be dosed sequentially, with a minimum interval of at least two days between dosing of consecutive subjects in order to provide an additional measure of safety assurance.

The first cohort will be allocated to d$_1$. The statistical model will be updated after complete toxicity information is available for each cohort. By rule, one additional cohort may be enrolled before complete information is available for all subjects on the most recent cohort. Incomplete toxicity data is allowed for no more than 3 patients before the next cohort is enrolled and randomized.

Each subsequent cohort will be assigned to the dose that is estimated to be the MTD according to the definition above. In the event of slow accrual, the model may be updated as each patient enrolls and each subsequent patient dosed to the current estimated MTD.

Study Population: This study will enroll male and female subjects with progressive supranuclear palsy (PSP) aged 50 to 85 years.

Inclusion Criteria: For inclusion into the study, each subject must be willing and able to provide informed consent. Prior to initiation of the treatment protocol, it will be confirmed that each subject is able to provide consent for the treatment protocol. Subjects will be invited to participate in the study, and after signing the informed consent form, screening procedures will take place. If subjects fail to fulfill the inclusion criteria or meet any of the exclusion criteria, the subjects will not be enrolled into the screening assessment or treatment schedule.

Each subject must meet the following criteria to be enrolled in this study: Male or female; Between 50 and 85 years of age; Meets NINDS-SPSP possible or probable criteria as modified for NNIPPS and AL-108-231 clinical trials, including: (d) supranuclear gaze palsy or decreased saccade velocity, (ii) gait instability or falls within the first 3 years of symptoms; Brain MRI at Screening is consistent with PSP (<4 microhemorrhages, and no large strokes or severe white matter disease); Score on the PSP rating scale between 20 and 50; Able to provide informed consent to participation at baseline or if unable to provide informed consent can provide assent to participation and has an authorized medical representative who can provide consent; Has study partner who sees the patient at least 5 hours per week, who can accompany the patient to visits and consents to study participation; Other concurrent non-biologic therapies are allowed but the dose must have been stable for at least 30 days prior to enrollment; Able to walk 5 steps with minimal assistance (stabilization of one arm or use of cane/walker); Stable medications for Parkinsonism for at least 2 months prior to Screening; including, levodopa, dopamine agonists, rasagaline, COMT inhibitors, amantadine, memantine or cholinesterase inhibitors; Agrees to up to 3 lumbar punctures over 4-18 months, up to 6 lumbar punctures if the subject will participate in both the phase 1/SAD study and the phase 2/MAD study; Signed and dated written informed consent obtained from the subject; Agree to use protocol specified methods of contraception (see below).

Subjects who meet any of the following criteria will be excluded from the study: Signs of a progressive neurological disorder that better meets the criteria for types of neurological disorders other than PSP, including: (a) meets criteria for probable Alzheimer's disease or (b) meets research criteria for Parkinson's Dementia with Lewy Bodies, multiple system atrophy (MSA), or amyotrophic lateral sclerosis (ALS); Any malignancy (other than non-metastatic basal cell carcinoma of the skin) within 5 years of screening; Clinically significant renal or hepatic dysfunction at screening based on professional judgment of Investigator; Clinically significant cardiovascular event within three months prior to study entry, based on professional judgment of Investigator; Clinically significant abnormal hematology or chemistry laboratory test results during screening, based on professional judgment of Investigator; Have received any prior monoclonal antibody therapy for any reason within the last 90 days or received any other investigational agent within the previous 30 days or 5 half-lives (whichever is longer). Prior administration of $C_2N$-8E12 does not apply to this exclusion criteria and, therefore, does not disqualify a subject from participating in the phase 2/MAD study; Currently on any other biologic or immunomodulatory therapy; Disease duration of greater than 5 years since onset of symptoms; Midbrain volume>8,600 mm$^3$ on screening MRI scan; Subjects that reside at a skilled nursing or dementia care facility; Has clear evidence of motor neuron disease on examination, consistent with ALS pathology (this has been described in C9ORF72 carriers with CBS presentation); Diagnosis of any other significant unrelated neurological or psychiatric disorders that could account for cognitive deficits (e.g., active seizure disorder, stroke, vascular dementia), based on professional judgment of Investigator; Untreated major depression at baseline evaluation, based on clinical judgment and results in GDS; History of other major psychiatric illness; Any prior history of suicidal attempts; Severe cognitive impairment as assessed by MMSE (<17) that in the Investigator's opinion would preclude collection of outcome measures; Not being able to participate in evaluation protocol; Significant, abnormal values in general from blood samples taken at screening that would pose a safety risk or interfere with appropriate interpretation of study data; Current or recent history (within four weeks prior to Screening) of a clinically significant bacterial, fungal, or mycobacterial infection; Unable to tolerate MRI scan at Screening or any other contraindication to MRI; Any contraindication to or unable to tolerate lumbar puncture at Screening, including use of anti-coagulant medications such as warfarin. Daily administration of 81 mg aspirin or similar anticoagulants will be allowed as long as the dose is stable for 30 days prior to Screening; Subjects who, in the opinion of the Investigator, are unable or unlikely to comply with the dosing schedule or study evaluations; Participation in another interventional clinical trial within 3 months of Screening; Treatment with another investigational drug within 30 days of Screening; Any preexisting QTcF duration exceeding 450 ms; Subject is employee or family member of the Sponsor or investigational site staff member or their family members.

Subjects must agree to use (and/or have their partner use) acceptable methods of contraception beginning at the baseline visit throughout the study and until 56 days after the last dose of study drug in the last treatment period. Acceptable methods of contraception are listed below.

Study drug: The phase 1/SAD study will use $C_2N$-8E12 from DP Lot #1018775—the Research Cell Bank (RCB) material currently being used in the Expanded Access IND 119404. It is formulated in 25 mM acetate buffer at pH 5.5, and it is provided at a concentration of 20 mg/mL. Placebo: Placebo is formulated identically to $C_2N$-8E12 without the active study drug.

Dose Rationale: The maximum recommended starting dose (MRSD) was calculated using the Food and Drug Administration (FDA) Guidance for Industry "Estimating the Safe Starting Dose in the Clinical Trials for Therapeutics in Adult Healthy Volunteers". Per the guidance, for investigational therapeutic proteins with molecular weight>100,000 Daltons that are administered IV, the MRSD should be estimated by normalizing across species instead of via body surface area scaling. Based upon the No Observed Effect Level (NOEL) observed of 250 mg/kg in the mouse toxicology study, a standard safety factor of 10 limits the dose to 25 mg/kg.

The starting dose for phase 1/SAD study will be 2.5 mg/kg dosed IV. This starting dose is 10 times lower than the maximally allowed starting dose based on a 4-week mouse toxicology study and 6 times lower than the current maximal dose (15 mg/kg) administered in the Expanded Access and compassionate use human treatment protocols involving $C_2N$-8E12 (see Investigator's Brochure).

Based on preliminary plasma PK from a single patient trial, it is possible to estimate the percent of tau in CSF that is bound by $C_2N$-8E12 at various times after a 2.5 mg/kg dose of $C_2N$-8EI2. For this calculation, it is assumed that the CSF concentration for a humanized antibodies is 0.1% of the plasma concentration and that the concentration of tau in CSF is 500 pg/mL. Based on these assumptions, a dose of 2.5 mg/kg will lead to a CSF concentration of $C_2N$-8E12 over the first month that is between 3 to 40 times higher than the molar concentration of tau in CSF. Based on the $K_D$ of $C_2N8E12$, the 2.5 mg/kg dose will lead to 3-26% of tau in CSF being bound by the antibody. Similar modeling has been performed on the PK data from the highest dose administered to humans to date (15 mg/kg) and estimated that the average tau binding over the 28 day period is around 50% (max 72% bound, min 40%). There will likely also be an abundance of extracellular tau present in the brain that is not accessible through the CSF compartment, but to which the antibody will be able to bind. Therefore, dose escalation will proceed to 25 mg/kg to assess safety of a dose that will likely lead to significant target engagement in the brain.

Unless approved by the Investigator, during the treatment period, no study subject should receive: Any other biologic or immunomodulatory therapy; Any other investigational agent; Warfarin; Any anticoagulant (other than 81 mg daily aspirin) for a condition for which temporary cessation of the treatment prior to CSF sampling would provide a medical hazard.

Informed Consent: After providing informed consent, each subject will undergo screening assessments to reconfirm that the inclusion criteria can be fulfilled, and that no contraindications exist to receiving treatment under this protocol. Specifically, each subject will be assessed at screening with a clinical and neurological examination to confirm the diagnosis. A brief cognitive screening with PSP ratings scale and a depression scale with interview will be made and a complete medical and drug/medication history will be obtained. If the subject fulfills all inclusion criteria and lacks exclusion criteria, further investigations will be performed. The Screening visit occurs 28 days to 7 days before the Baseline/Day 0 Visit.

Pharmacokinetic Assessments: Samples will be collected for PK analysis at various time points described in Table 3 below.

CSF sampling with measurement of cell counts (WBC and RBC), total protein and glucose.

Determination of C2N-8E12 in human plasma and CSF: Sandwich ELISA assays have been developed for measuring the concentration of C2N-8E12 in plasma and CSF. Charles River Laboratories has validated these assays for use in a variety of different matrices (See Table 4).

TABLE 4

| CRL Study # | Study Title |
| --- | --- |
| 20056682 Completed | Validation of an Enzyme-Linked Immunosorbent Assay (ELISA) Method for the Determination of $C_2N$-8E12 in Human Plasma (K2EDTA) |
| 20057088 Ongoing | Validation of an Enzyme-Linked Immunosorbent Assay (ELISA) Method for the Determination of $C_2N$-8E12 in Human Cerebrospinal Fluid |

Determination of anti-C2N-8E12 antibodies in human plasma: Blood samples will be collected for assessment of anti-drug antibody (ADA) development prior to initial dosing and on day 14 and 28 post-administration of drug. A final measurement will occur at termination. An ECL based sandwich ELISA assay has been developed for measuring the presence of antibodies against $C_2N$-8E12 in plasma (ADA). Charles River Laboratories has validated this assay for detection of ADA response in human plasma (See Table 5).

TABLE 5

| CRL Study # | Study Title |
| --- | --- |
| 20056686 Complete | Validation of a Qualitative Electrochemiluminesent (ECL) Assay for the Detection of anti-$C_2N$-8E12 Antibodies in Human Plasma (K2EDTA) |

Clinical and functional assessments include Colombia-Suicide Severity Rating Scale: As a safety parameter, the

TABLE 3

| Pre-dose | 15 min (#) | 3 hrs | 6 hrs | 12 hrs | 24 hrs | 48 hrs | 168 hrs | 336 hrs | 28 days | Post 28 day |
| --- | --- | --- | --- | --- | --- | --- | --- | --- | --- | --- |
| X | X | X | X | X | X | X | X | X | X | (@) |

(*) If an early termination occurs, a final blood sample will be obtained at the Early Termination Visit for final PK assessment;
(#) Within 15 minutes of infusion completion;
(@) Post day 28, PK samples will be taken every 28 days until the earlier occurrence of either of the following events: (i) study termination; (ii) the absence of any detectable blood levels of $C_2N$-8E12.

Adverse Events Assessments: The following safety assessment will be conducted in order to monitor for AEs: Vital signs (blood pressure, pulse/heart rate, temperature, respiratory rate, SPO2); Complete neurologic exam, including a cognitive assessment (mental status tests); Laboratory tests: (1) Hematology panel: complete blood count (CBC) with differential, hematocrit, and hemoglobin (Hb), platelet count; (2) Chemistry panel: serum electrolytes, glucose, uric acid, blood urea nitrogen (BUN), creatinine, total protein, albumin, bilirubin (total, direct and indirect), alkaline phosphatase, lactate dehydrogenase (LDH), liver enzymes (AST, ALT and GGT), iron, cholesterol panel, CPK, amylase, and lipase; (3) Coagulation panel: Prothrombin Time (PT), INR, and Partial Thromboplastin Time (PIT); Urinalysis, including measurement of Hb, WBC, and protein content; ECG—continuous monitoring or 12 lead ECG; MRI brain imaging, including fluid attenuated inversion recovery (FLAIR); A Columbia-Suicide Severity Rating Scale (C-SSRS) for suicidal ideation will be used (Posner et al. 2011). Geriatric Depression Scale: Similar to the C-SSRS, the Geriatric Depression Scale (GDS) will be used to assess overall mood during the study. The Geriatric Depression Scale (GDS) is a 30-item self-report assessment used to identify depression in the elderly (Yesavage et al. 1983). PSP Rating Scale: The PSP Rating Scale (PSPRS) will be used at screening for inclusion as well as baseline and end of the study to assess changes in the scale over time (Golbe and Ohman-Strickland 2007). Clinical Global Impressions: The clinical Global Impressions rate of change (CGIc) and severity (CGIs) scales will be used to assess severity of symptoms. Schwab and England Activities of Daily Living: The Schwab and England Activities of Daily Living (SEADL) scale will be used as a means of assessing the subjects ability to perform daily activities (Schwab and England 1969). Clinical Dementia Rating Sum of Boxes Frontotemporal Lobe Dementia: The Clinical Dementia Rating Sum of Boxes Frontotemporal Lobe Dementia (CDR-SB-FTLD) is a version of the CDR-SB cognitive assessment test that includes assessment of behavior, comportment, personality, and language (Knopman et al. 2008). Mini Mental State Examination: The mini mental state examination (MMSE) is a reliable 30-point questionnaire that measures cognitive impairment (Folstein, Folstein, and McHugh 1975).

Cerebrospinal fluid: CSF will be drawn from the L3-4 interspace by lumbar puncture. If CSF sampling is not successful CT/fluoro guided lumbar puncture can be used at the discretion of the local clinical site staff as per local protocol. Safety labs on CSF will be analyzed locally at the applicable clinical site after each lumbar puncture/CSF collection. These measures include: cell counts (WBC and RBC), total protein and glucose. Other CSF measurements (e.g., C2N-8E12 concentration, target engagement and other exploratory biomarkers) will be analyzed by the applicable designated laboratory.

Imaging: The subject will also receive a baseline MRI scan with structural, FLAIR, diffusion-weighted and susceptibility weighted imaging. Post-dosing imaging analyses will be performed according to the Schedule of Events.

Exploratory pharmacogenomic analysis: A blood sample will be collected for DNA extraction at baseline. All individuals will undergo an extended MAPT haplotype sequence analysis to determine H1(A-D) and H2 carrier status. DNA will be extracted from the samples and the DNA shipped to the designated pharmacogenomic core for this study.

Subjects will be enrolled in this study until the earlier occurrence of any of the following events: (i) they complete their participation and the entire Schedule of Events; (ii) they or the Investigator decide(s) to terminate their participation; or (iii) the applicable subject experiences any DLT or any SAE that an Investigator deems to preclude further participation in this study and precludes eligibility for the subsequent phase 2/MAD study. Additionally, at the discretion of the Investigator, subjects who cease to meet any inclusion criterion, or meet one or more exclusion criterion during the study, may be determined ineligible to continue participating in the study or for subsequent participation in the phase 2/MAD study.

We claim:

1. An isolated monoclonal anti-tau antibody comprising a light chain comprising the amino acid sequence of SEQ ID NO: 2, and a heavy chain comprising the amino acid sequence of SEQ ID NO: 5.

2. The antibody of claim 1, wherein the antibody is a humanized IgG1, IgG2, IgG3, or IgG4 antibody.

3. The antibody of claim 1, wherein the antibody is a humanized IgG4 antibody containing a S241P hinge stabilizing mutation.

4. The antibody of claim 1, wherein the antibody binds an epitope comprising an amino acid sequence of SEQ ID NO: 9.

5. A pharmaceutical composition comprising the anti-tau antibody of claim 1 and a pharmaceutically acceptable carrier.

6. An isolated monoclonal anti-tau antibody comprising a light chain comprising the amino acid sequence of SEQ ID NO: 18; and a heavy chain comprising the amino acid sequence of SEQ ID NO: 13.

7. A pharmaceutical composition comprising the anti-tau antibody of claim 6 and a pharmaceutically acceptable carrier.

8. The antibody of claim 6, wherein the antibody binds an epitope comprising an amino acid sequence of SEQ ID NO: 9.

9. A nucleic acid molecule encoding an antibody light chain comprising the amino acid sequence of SEQ ID NO: 2, and an antibody heavy chain comprising the amino acid sequence of SEQ ID NO: 5.

10. The nucleic acid molecule of claim 9 that encodes a light chain comprising the amino acid sequence of SEQ ID NO: 18, and a heavy chain comprising the amino acid sequence of SEQ ID NO: 13.

11. The antibody of claim 1, wherein the antibody comprises a light chain constant region of human isotype kappa.

12. A pharmaceutical composition comprising the anti-tau antibody of claim 3 and a pharmaceutically acceptable carrier.

* * * * *

UNITED STATES PATENT AND TRADEMARK OFFICE
CERTIFICATE OF CORRECTION

PATENT NO. : 9,957,317 B2  
APPLICATION NO. : 15/257086  
DATED : May 1, 2018  
INVENTOR(S) : Tim West et al.

Page 1 of 1

It is certified that error appears in the above-identified patent and that said Letters Patent is hereby corrected as shown below:

In the Drawings

On sheet 1 of 17, in Fig. 1, in the light chain sequences identified as VK1, VK2, and VK3, respectively, replace -QFP- with -QPP-.

On sheet 3 of 17, in Fig. 2H, replace -DIVLTQ- with -DIVMTQ-.

In the Specification

Please replace the paragraph starting at Column 1, Line 6, with the following paragraph:
-This application is a continuation of International Application No. PCT/US2015/038002, filed on Jun. 26, 2015, which claims benefit of priority under 35 U.S.C. § 119(e) of U.S. Ser. No. 62/170,036, filed Jun. 2, 2015, U.S. Ser. No. 62/080,903, filed Nov. 17, 2014, and U.S. Ser. No. 62/018,436, filed Jun. 27, 2014, the entire contents of which are incorporated herein by reference in their entirety.-.

Please replace the paragraph starting at Column 1, Line 16, with the following paragraph:
-The instant application contains a Sequence Listing which has been submitted electronically in ASCII format on April 6, 2017, and is hereby incorporated by reference in its entirety. Said ASCII copy, created on April 6, 2017, is named 397835-215C1(156248)_SL.txt and is 42,533 bytes in size.-.

Signed and Sealed this  
Fifth Day of November, 2019

Andrei Iancu  
*Director of the United States Patent and Trademark Office*